(12) United States Patent
Kim et al.

(10) Patent No.: US 12,180,459 B2
(45) Date of Patent: Dec. 31, 2024

(54) *KAZACHSTANIA TURICENSIS* CAU Y1706 AND COMPOSITION USING SAME

(71) Applicant: CHUNG ANG UNIVERSITY INDUSTRY ACADEMIC COOPERATION FOUNDATION, Seoul (KR)

(72) Inventors: Won Yong Kim, Seoul (KR); Jong Hwa Kim, Seoul (KR); Ki Young Kim, Seoul (KR); Kanjanasuntree Rungravee, Seoul (KR)

(73) Assignee: CHUNG ANG UNIVERSITY INDUSTRY ACADEMIC COOPERATION FOUNDATION, Seoul (KR)

( * ) Notice: Subject to any disclaimer, the term of this patent is extended or adjusted under 35 U.S.C. 154(b) by 608 days.

(21) Appl. No.: 17/425,079

(22) PCT Filed: Jan. 23, 2020

(86) PCT No.: PCT/KR2020/001222
§ 371 (c)(1),
(2) Date: Jul. 22, 2021

(87) PCT Pub. No.: WO2020/153815
PCT Pub. Date: Jul. 30, 2020

(65) Prior Publication Data
US 2022/0106559 A1 Apr. 7, 2022

(30) Foreign Application Priority Data
Jan. 23, 2019 (KR) .................. 10-2019-0008823

(51) Int. Cl.
| | | |
|---|---|---|
| *C12N 1/16* | (2006.01) | |
| *A23L 31/15* | (2016.01) | |
| *A61K 8/9728* | (2017.01) | |
| *A61K 36/06* | (2006.01) | |
| *A61P 17/00* | (2006.01) | |
| *A61Q 19/00* | (2006.01) | |

(52) U.S. Cl.
CPC .............. *C12N 1/16* (2013.01); *A23L 31/15* (2016.08); *A61K 8/9728* (2017.08); *A61K 36/06* (2013.01); *A61P 17/00* (2018.01); *A61Q 19/00* (2013.01)

(58) Field of Classification Search
None
See application file for complete search history.

(56) References Cited

U.S. PATENT DOCUMENTS

| | | | | |
|---|---|---|---|---|
| 2011/0123640 A1* | 5/2011 | Yabumoto | ............... | A61P 31/00 |
| | | | | 435/252.9 |
| 2019/0183950 A1* | 6/2019 | Way | ........................ | A61P 37/02 |

FOREIGN PATENT DOCUMENTS

| | | |
|---|---|---|
| KR | 10-2007-0076378 | 7/2007 |
| KR | 10-2011-0036036 | 4/2011 |

OTHER PUBLICATIONS

Bourrie et al., "The Microbiota and Health Promoting Characteristics of the Fermented Beverage Kefir", Frontiers in Microbiology, vol. 7, Article 647, pp. 1-17 (Year: 2016).*
Rosa et al., "Milk kefir: nutritional, microbiological and health benefits", Nutrition Research Reviews, vol. 30, pp. 82-96 (Year: 2017).*
Wang et al., "Identification of Yeasts and Evaluation of their Distribution in Taiwanese Kefir and Viili Starters", Journal of Dairy Science, vol. 91, pp. 3798-3805 (Year: 2008).*
Leite et al., "Microbiological, Technological and Therapeutic Properties of Kefir: A Natural Probiotic Beverage", Brazilian Journal of Microbiology, Sep. 2012, pp. 341-349.
Kim et al., "Kazachstania Turicensis CAU Y1706 Ameliorates Atopic Dermatitis by Regulation Of The Gut-Skin Axis", J Dairy Sci. Feb. 2019, pp. 2854-2862.
Mainville et al., "Accurate Identification of Yeasts in Kefir by Polyphasic Analysis", EC Microbiology, Sep. 2017, pp. 104-113.
Wyder et al., "Description of *Saccharomyces turicensis* sp. nov., A Aew Species from Kefyr", Systematic and Applied Microbiology, May 1999, pp. 420-425.
International Search Report dated May 7, 2020 for International Application No. PCT/KR2020/001222, 5 pages.

* cited by examiner

*Primary Examiner* — Michelle F. Paguio Frising
(74) *Attorney, Agent, or Firm* — Bochner PLLC; Andrew Bochner; Eric Kleinertz

(57) ABSTRACT

The present invention relates to a novel *Kazachstania turicensis* CAU Y1706 and a composition using same, and more specifically, to a *Kazachstania turicensis* CAU Y1706 (Accession No.: KCTC13794BP) strain, and a pharmaceutical composition, a food composition, a cosmetic composition, and a probiotic composition for preventing or treating inflammatory diseases, comprising the strain or a culture thereof as an active ingredient.

10 Claims, 26 Drawing Sheets

KAZACHSTANIA TURICENSIS CAU Y1706 AND COMPOSITION USING SAME

TECHNICAL FIELD

This application claims priority to Korean Patent Application No. 10-2019-0008823 filed on Jan. 13, 2018, and the entire specifications of which are incorporated herein by reference in their entireties.

The present invention relates to a novel *Kazachstania turicensis* CAU Y1706 and a composition using same, and more specifically, to a *Kazachstania turicensis* CAU Y1706 (Accession No.: KCTC13794BP) strain, and a pharmaceutical composition, a food composition, a cosmetic composition, and a probiotic composition for preventing or treating inflammatory diseases, comprising the strain or a culture thereof as an active ingredient.

BACKGROUND OF THE INVENTION

Inflammation is a continuous and complex reaction that destroys the cells that make up the body. Inflammatory reaction refers to a pathological condition formed by the invasion of external infectious agents (bacteria, fungi, viruses, and various allergens), and this is a defense reaction process of the living body that tries to repair and regenerate the damaged area when an invasion that causes any organic change is applied to the cells or tissues of the living body.

In general, the inflammatory response is a biological defense mechanism to regenerate damage caused by invasion that causes any organic change in cells or tissues of the living body, and local blood vessels, various tissue cells of body fluids, and immune cells act in this reaction process. The inflammatory response normally induced by external invading bacteria is a defense action to protect the living body, whereas when an abnormally excessive inflammatory response is induced, various diseases appear.

Asthma, one of the chronic inflammatory diseases, is caused by airway hyperresponsiveness, deposition of inflammatory cells into lung tissue, and excessive production of mucus, and allergic asthma is induced by overexpression of cytokines including interleukin (IL)-4, IL-5, and IL-13 and chemokines such as eotaxin and lentis. Mast cells and eosinophils cells produce various inflammation-inducing mediators in B cells, activated immune cells. Eosinophilic cells increase particulate proteins and generate reactive oxygen species as basic mediators of asthma development.

Allergy is a systemic or local disorder of a living body based on an immune response as a summation of a wide range of complex pathological phenomena. Allergies appearing in the human body are classified into I, II, III, and IV types according to the immune mechanism, and among them, type I allergy, which is an immediate hypersensitivity reaction, occupies an important part in clinical practice, and these include atopic dermatitis, allergic rhinitis, bronchial asthma, hay fever and pollinosis etc.

Asthma, known as the representative disease of type I allergy, is mostly an allergic disease, and clinical symptoms such as wheezing, shortness of breath, and cough caused by extensive stenosis of the airways can be improved spontaneously or reversibly with treatment. The number of deaths due to asthma is increasing worldwide, and in developing countries 3-10% suffer from asthma.

In addition, when the skin is exposed to an allergen, antigen-specific IgE binds to the IgE receptor on the surface of Langerhans cells, and this antigen is delivered to the T cells on the surface and the T cells are activated. In this case, unlike normal, in allergic skin diseases, especially Th2 is activated in atopic dermatitis, and cytokines such as IL-4, IL-5, IL-6, IL-8, IL-10 and IL-13 are secreted, and the production of IgE in B cells is promoted as a result, and inflammatory cytokines and histamine are released by promoting degranulation of activated mast cells.

However, so far, there have been few reports on the effects of probiotic yeast on inflammatory diseases, allergies, especially atopic dermatitis.

Kefir is a dairy product made by symbiotic fermentation of lactic acid bacteria and yeast in milk, and is a well-known probiotic food. *Kazachstania turicensis*, belonging to the kefir yeast, formerly known as *Saccharomyces turicensis*, is isolated from various kefir grains (System. Apple. Microbiol. 22, 420-425 (1999)).

However, the therapeutic effect and immunomodulatory ability of *Kazachstania turicensis*, a yeast isolated from kimchi, a traditional Korean food, and its inflammatory diseases have not been reported.

DETAILED DESCRIPTION OF THE INVENTION

Technical Problem

Accordingly, the present inventors have completed the present invention by isolating a novel *Kazachstania turicensis* CAU Y1706 that modulates the immune response and is excellent in the ability to modulate the immune response and change the intestinal microbial group in an ovalbumin (OVA)-sensitized AD mouse model.

Therefore, an object of the present invention is to provide *Kazachstania turicensis* CAU Y1706 (Accession No: KCTC13794BP) strain.

Another object of the present invention is to provide a pharmaceutical composition for the preventing or treating an inflammatory disease comprising the strain or a culture thereof as an active ingredient.

In addition, it is to provide a pharmaceutical composition for the preventing or treating an inflammatory disease (essentially) consisting of the strain or a culture thereof as an active ingredient.

Another object of the present invention is to provide a food composition for preventing or improving an inflammatory disease comprising the strain or a culture thereof as an active ingredient.

In addition, it is to provide a food composition for the preventing or improving an inflammatory disease (essentially) consisting of the strain or a culture thereof as an active ingredient.

Another object of the present invention is to provide a cosmetic composition for preventing or improving an inflammatory disease comprising the strain or a culture thereof as an active ingredient.

In addition, it is to provide a cosmetic composition for preventing or improving an inflammatory disease (essentially) consisting of the strain or a culture thereof as an active ingredient.

Another object of the present invention is to provide an enteral composition comprising the strain or a culture thereof as an active ingredient.

In addition, it is to provide an enteral composition comprising (essentially) the strain or a culture thereof as an active ingredient.

Another object of the present invention is to provide a probiotic composition comprising the strain or a culture thereof as an active ingredient.

In addition, it is to provide a probiotic composition (essentially) consisting of the strain or a culture thereof as an active ingredient.

Another object of the present invention is to provide an immunomodulatory composition comprising the strain or a culture thereof as an active ingredient.

In addition, it is to provide an immunomodulatory composition (essentially) consisting of the strain or a culture thereof as an active ingredient.

Another object of the present invention is to provide a food additive composition comprising the strain or a culture thereof as an active ingredient.

In addition, it is to provide a food additive composition (essentially) consisting of the strain or a culture thereof as an active ingredient Another object of the present invention is to provide use of the strain or a culture thereof for preparing an agent for the prevention or treatment of inflammatory diseases.

Another object of the present invention is to provide a method for treating an inflammatory disease comprising administering to a subject in need thereof an effective amount of a composition comprising the strain or a culture thereof as an active ingredient.

Another object of the present invention is to provide use of the strain or a culture thereof for the production of a probiotic agent.

Another object of the present invention is to provide use of the strain or a culture thereof for preparing an enteral agent.

Another object of the present invention is to provide use of the strain or a culture thereof for preparing an immunomodulatory agent.

Another object of the present invention is to provide a method of immunomodulation comprising administering to a subject in need thereof an effective amount of a composition comprising the strain or a culture thereof as an active ingredient.

Another object of the present invention is to provide use of the strain or a culture thereof for preparing a food additive agent.

Technical Solution

In order to achieve the above object, the present invention provides a *Kazachstania turicensis* CAU Y1706 (Accession number: KCTC13794BP) strain.

In order to achieve another object of the present invention, the present invention provides a pharmaceutical composition for preventing or treating an inflammatory disease comprising the strain or a culture thereof as an active ingredient.

In addition, the present invention provides a pharmaceutical composition for preventing or treating an inflammatory disease (essentially) consisting of the strain or a culture thereof as an active ingredient.t In order to achieve another object of the present invention, the present invention provides a food composition for preventing or improving an inflammatory disease comprising the strain of or a culture thereof as an active ingredient.

In addition, the present invention provides a food composition for preventing or improving an inflammatory disease (essentially) consisting of the strain of or a culture thereof as an active ingredient.

In order to achieve another object of the present invention, the present invention provides a cosmetic composition for preventing or improving an inflammatory disease comprising the strain or a culture thereof as an active ingredient.

In addition, the present invention provides a cosmetic composition for preventing or improving an inflammatory disease (essentially) consisting of the strain or a culture thereof as an active ingredient.

In order to achieve another object of the present invention, the present invention provides an enteral composition comprising the strain or a culture thereof as an active ingredient.

In addition, the present invention provides an enteral composition (essentially) consisting of the strain or a culture thereof as an active ingredient.

In order to achieve another object of the present invention, the present invention provides a probiotic composition comprising the strain or a culture thereof as an active ingredient.

In addition, the present invention provides a probiotic composition (essentially) consisting of the strain or a culture thereof as an active ingredient.

In order to achieve another object of the present invention, the present invention provides an immunomodulatory composition comprising the strain or a culture thereof as an active ingredient.

In addition, the present invention provides an immunomodulatory composition (essentially) consisting of the strain or a culture thereof as an active ingredient.

In order to achieve another object of the present invention, the present invention provides a food additive composition comprising the strain or a culture thereof as an active ingredient.

In addition, the present invention provides a food additive composition (essentially) consisting of the strain or a culture thereof as an active ingredient.

In order to achieve another object of the present invention, the present invention provides use of the strain or a culture thereof for preparing an agent for the prevention or treatment of inflammatory diseases.

In order to achieve another object of the present invention, the present invention provides a method for treating an inflammatory disease comprising administering to a subject in need thereof an effective amount of a composition comprising the strain or a culture thereof as an active ingredient.

In order to achieve another object of the present invention, the present invention provides use of the strain or a culture thereof for the production of a probiotic agent.

In order to achieve another object of the present invention, the present invention provides use of the strain or a culture thereof for preparing an enteral agent.

In order to achieve another object of the present invention, the present invention provides use of the strain or a culture thereof for preparing an immunomodulatory agent.

In order to achieve another object of the present invention, the present invention provides a method of immunomodulation comprising administering to a subject in need thereof an effective amount of a composition comprising the strain or a culture thereof as an active ingredient.

In order to achieve another object of the present invention, the present invention provides use of the strain or a culture thereof for preparing a food additive agent.

Hereinafter, the present invention will be described in detail.

The present invention provides a *Kazachstania turicensis* (accession number: KCTC13794BP) strain.

The *Kazachstania turicensis* is a strain, characterized in that it has anti-inflammatory activity, in particular, it is characterized by improving the imbalance of Th1/Th2 immune response, especially the immune response imbalance of excessive Th2 immune response, by increasing the Th1 cytokine level and decreasing the Th2 cytokine level.

The present inventors isolate the strain of the present invention from kimchi, and a novel yeast *Kazachstania turicensis* CAU Y1706 that inhibits Th2 cytokines was selected by significantly reducing the concentration of Th2 cytokines such as IL-4 and ILS, increasing the level of Th1 cytokines such as IFN-γ, TNF-α, and IL-12, and also decreasing the Treg cytokine level. As a result of molecular biological analysis using the 18s and 26s rRNA nucleotide sequences, the selected strain was confirmed to be a novel *Kazachstania turicensis* yeast, and was named CAU Y1706. This strain was deposited on Jan. 22, 2019 at the Korea Research Institute of Bioscience and Biotechnology Biological Resources Center (KCTC) (Accession number: KCTC13794BP).

The *Kazachstania turicensis* according to the present invention is conventionally called *Saccharomyces turicensis* and is known as a yeast present in kefir grains of healthy fermented milk.

According to an embodiment of the present invention, it was confirmed that the novel yeast of the present invention not only regulates immune cytokines, but also reduces IgE, eosinophils, neutrophils, and basophils in serum, and also regulates the intestinal microbial flora.

According to another embodiment of the present invention, the novel yeast of the present invention exhibited an effect of improving inflammation in the skin and intestines with respect to a model using an ovalbumin-sensitized mouse. Specifically, it was confirmed that it suppressed the accumulation of mast cells in the skin cells of the back and ileum and also decreased the number of eosinophils. In addition, it was confirmed that the level of eosinophil infiltration in the skin of the back was also reduced.

In addition, it was confirmed that the novel yeast according to the present invention has excellent acid resistance and bile resistance.

In an example of the present invention, an experiment was conducted under pH 2.0 conditions to confirm the acid resistance of the novel yeast, but as the number of yeast bacteria of the present invention increased at a significant rate over time, it was confirmed that the yeast of the present invention was not inhibited under strong acid conditions. In addition, the bacteria exhibited excellent growth ability even under the conditions of 0.2% and 0.4% bile acid.

In short, the novel yeast according to the present invention is not only excellent in anti-inflammatory, particularly in reducing skin inflammation, but also has a bowel effect, and excellent acid resistance and bile resistance, so it can reach the intestines and therefore has high commercial use value.

Accordingly, the present invention provides a pharmaceutical composition for preventing or treating an inflammatory disease comprising the strain or a culture thereof as an active ingredient.

As used herein, the term "comprising" has the same meaning as "including" or "characterized by", and in the composition or method according to the present invention, additional components or steps of the method not specifically mentioned are not excluded. In addition, the term "consisting of" means excluding additional elements, steps, or ingredients not specifically described. The term "essentially consisting of" means that, in the scope of a composition or method, it may include substances or steps that do not substantially affect the basic properties thereof in addition to the substances or steps described. '*Kazachstania turicensis* CAU Y1706' or '*Kazachstania turicensis* CAU Y1706 cells' according to the present invention include live cells isolated or purified from the culture medium, as well as any processed form (especially the processed form of live cells) of lactic acid bacteria known to those skilled in the art. Examples include, but are not limited to its form, a dried product, a frozen product, and the like. In addition, one or more compounds that are easily compatible with the strain in the culture medium may be mixed, or may be used in an unmixed form.

In addition, the strain according to the present invention may be used in a live form, a semi-active form, an inactivated form, or a dead form, but a live form is preferable. When using the strain according to the present invention in a dead form, it can be selected and used without limitation as long as it is by a method for killing lactic acid bacteria known in the art.

In the present invention, 'cultivation' means all actions performed to grow microorganisms in an appropriately artificially controlled environment, and in the present invention, as a concept including 'fermentation', 'culture product' is meant to include 'fermented product', and it includes processed products derived from the culture solution itself, such as the culture solution cultured in the medium (that is, the culture medium itself containing the bacteria), or the result of processing the culture solution such as heat treatment.

In addition, in the present invention, the inflammatory disease is a Th1-mediated immune disease or a Th2-mediated immune disease, more specifically, it may be any one or more diseases selected from the group consisting of acute or chronic organ transplant rejection, graft-versus-host disease, inflammatory bowel disease, Crohn's disease, ulcerative colitis, inflammatory skin disease, multiple sclerosis, pancreatitis, trauma-induced shock, bronchial asthma, allergic rhinitis, allergic conjunctivitis, cystic fibrosis, acute bronchitis, chronic bronchitis, acute bronchiolitis, chronic bronchiolitis, osteoarthritis, gout, spondyloarthropathy, ankylosing spondylitis, Reiter's syndrome, psoriatic arthropathy, enteric spondylitis, juvenile arthritis, juvenile ankylosing spondylitis, reactive arthropathy, infectious arthritis, postinfectious Arthritis, Lou Gehrig's disease, polyarteritis nodosa, hypersensitivity vasculitis, granulomatosis Lou Gehrig's disease, polymyalgia rheumatica, articular cell arteritis, calcium crystallization arthropathy, pseudo gout, non-articular rheumatism, bursitis, tendinitis, epicondylitis, neuropathic joint Diseases (neuropathic joint disease or charcot joint), hemarthrosis, allergic purpura, hypertrophic osteoarthropathy, multicentral reticulocytoma, scoliosis, hemochromatosis, hemoglobinopathy, hyperproteinemia, hypogammaglobulinemia, familial Mediterranean fever, Behcet's disease, systemic lupus erythematosus, recurrent fever, sepsis, septic shock, acute respiratory distress syndrome, multiple organ failure, chronic obstructive pulmonary disease, rheumatoid arthritis, acute lung injury, broncho-pulmonary dysplasia, type 1 diabetes, type 2 diabetes, arteriosclerosis, Alzheimer's dementia, familial cold autoinflammatory syndrome, Muckle-Wells syndrome, neonatal multisystem inflammatory disease, chronic infantile neurologic cutaneous articular syndrome, adult-onset Still's disease, contact dermatitis, hydatidiform mole, PAPA syndrome (syndrome of pyogenic arthritis, pyoderma gangrenosum and acne), hyperimmunoglobulin d syndrome, cryopyrin-associated periodic syndrome, keratitis, conjunctivitis, retinitis, retinal vasculitis, uveitis, blepharitis, allergic conjunctivitis, dry eye, progressive systemic sclerosis, polymyositis, autoimmune encephalomyelitis, myasthenia gravis, polyarteritis nodosa and fibromyalgia syndrome.

As used herein, "transplant rejection" may be, specifically, acute or chronic transplant rejection that occurs after transplantation of solid organs such as heart, lung, heart and lung complex, liver, kidney, pancreas, skin, bowel or acute or cornea, resulting in apoptosis and tissue necrosis caused by infiltrating and attacking the transplanted organ by immune cells in the transplanted patient's body, and graft-versus-host disease (GVHD) after bone marrow transplantation.

Among the inflammatory diseases, the inflammatory skin disease is one or more diseases selected from the group consisting of psoriasis, atopic dermatitis, dermatitis eczema, contact dermatitis, seborrheic dermatitis, pneumoconiosis rosacea, lichen planus, vasculitis, pityriasis pilaris, cellulitis, folliculitis, pemphigus, pemphigus, bullous pemphigus, epidermal blistering, urticaria, angioedema, vasculitis, erythema and cutaneous eosinophilia.

As used herein, the term "prevention" refers to any action that inhibits or delays the onset of degenerative brain disease by administration of the pharmaceutical composition according to the present invention, "treatment" refers to any action in which the symptoms of the suspected and onset subject of degenerative brain disease are improved or beneficially changed by administration of the pharmaceutical composition.

In the present invention, the content of the composition is not significantly limited depending on the purpose or aspect of use, for example, it may be 0.01 to 99% by weight, preferably 0.5 to 50% by weight, more preferably 1 to 30% by weight based on the total weight of the composition. In addition, the pharmaceutical composition according to the present invention may further include an additive such as a pharmaceutically acceptable carrier, excipient or diluent in addition to the active ingredient.

The pharmaceutical composition according to the present invention may include the strain alone in a pharmaceutically effective amount or may further include one or more pharmaceutically acceptable carriers. The pharmaceutical composition of the present invention may be administered to a patient as a single dose, and may be administered by a fractionated treatment protocol in which multiple doses are administered for a long period of time. In the above, the pharmaceutically effective amount refers to an amount that exhibits a higher response than the negative control, and preferably refers to an amount sufficient to treat or prevent degenerative brain disease. The effective amount of the strain according to the present invention may be 0.001 to 1000 mg/kg b.w./day, preferably 1 to 2000 mg/kg b.w./day, but is not limited thereto. However, the pharmaceutically effective amount may be appropriately changed according to various factors such as the disease and its severity, the patient's age, weight, health status, sex, administration route, and treatment period.

The composition of the present invention may be formulated in various ways according to the route of administration by methods known in the art together with the pharmaceutically acceptable carrier.

The pharmaceutical composition of the present invention may be administered orally or parenterally to mammals including humans according to a desired method, and parenteral administration methods include external application to the skin, intraperitoneal injection, rectal injection, subcutaneous injection, intravenous injection, intramuscular injection, or intrathoracic injection and the like.

In the above, "pharmaceutically acceptable" refers to a non-toxic composition that does not inhibit the action of the active ingredient and does not normally cause gastrointestinal disorders, allergic reactions such as dizziness, or similar reactions, when physiologically acceptable and administered to humans. The composition of the present invention may be formulated in various ways according to the route of administration by methods known in the art together with the pharmaceutically acceptable carrier. The route of administration is not limited thereto, but may be administered orally or parenterally, preferably oral administration.

When the pharmaceutical composition of the present invention is orally administered, the pharmaceutical composition of the present invention may be formulated in the form of a powder, granules, tablets, pills, dragees, capsules, liquids, gels, syrups, suspensions, wafers etc. according to a method known in the art together with a suitable carrier for oral administration. For example, oral preparations include tablets, pills, powders, granules, capsules, and the like, and tablets or dragees can be obtained by combining the active ingredient with solid excipients, grinding them, adding suitable auxiliaries, and processing them into a mixture of granules. Examples of suitable excipients may be included saccharides including lactose, dextrose, sucrose, sorbitol, mannitol, xylitol, erythritol, and maltitol; starches, including corn starch, wheat starch, rice starch and potato starch; cellulose, including cellulose, methyl cellulose, sodium carboxymethyl cellulose and hydroxypropylmethyl-cellulose, and the like; fillers such as gelatin, polyvinylpyrrolidone, and the like. In addition, cross-linked polyvinylpyrrolidone, agar, alginic acid or sodium alginate etc. may be added as a disintegrant if necessary. Furthermore, the pharmaceutical composition of the present invention may further include an anti-aggregating agent, a lubricant, a wetting agent, a flavoring agent, an emulsifying agent, and an antiseptic agent etc.

In addition, when administered parenterally, the pharmaceutical composition of the present invention may be formulated according to a method known in the art together with a suitable parenteral carrier. Agents for parenteral administration may include sterile aqueous solutions, non-aqueous solutions, suspensions, emulsions, freeze-dried preparations, and suppositories. Non-aqueous solvents and suspensions may include propylene glycol, polyethylene glycol, vegetable oils such as olive oil, and injectable esters such as ethyl oleate. As other pharmaceutically acceptable carriers, those known in the art may be referred to.

As the base of the suppository, witepsol, macrogol, tween 61, cacao butter, laurin, glycero geratin and the like may be used.

Furthermore, the pharmaceutical composition of the present invention may be administered in parallel with a known compound having an effect of preventing and treating degenerative brain disease.

Furthermore, it can be preferably formulated according to each disease or component using an appropriate method in the art or a method disclosed in Remington's Pharmaceutical Science (latest edition), Mack Publishing Company, Easton PA.

In addition, the present invention provides a cosmetic composition for preventing or improving an inflammatory disease comprising the strain or a culture thereof as an active ingredient.

The cosmetic composition according to the present invention may be prepared in any formulation conventionally prepared in the art, and in addition to the novel strain or culture thereof according to the present invention, in the form of a basic cosmetic composition (lotion water, cream, essence, cleansing foam and cleansing water such as face wash, pack, body oil, mist, soap), a color cosmetic composition (foundation, lipstick, mascara, makeup base), a hair product composition (shampoo, conditioner, hair conditioner, hair gel), and a soap, etc. which are conventionally prepared in the field of dermatology with a dermatologically acceptable medium, base, auxiliary, excipient, etc. can be manufactured.

The excipient is not limited thereto, but may include, for example, an emollient, skin penetration enhancers, colorants, fragrances, emulsifiers, emollients, thickeners, thickeners, gelling agents, suspending agents, stabilizers, foaming agents, surfactants, fillers or solvents. In addition, it may further include a fragrance, a colorant, a bactericide, an antioxidant, a preservative, an auxiliary agent, and a moisturizing agent, and it may include thickeners, inorganic salts, synthetic polymers, and the like for the purpose of improving physical properties. For example, when preparing a face wash and soap with the cosmetic composition of the present invention, it can be easily prepared by adding the extract of the present invention to a conventional face wash and soap base. In the case of preparing a cream, it can be prepared by adding the strain of the present invention or a culture thereof to a general oil-in-water type (O/W) cream base. Here, synthetic or natural materials such as proteins, minerals, vitamins, etc. for the purpose of improving physical properties with fragrances, chelating agents, pigments, antioxidants, and preservatives may be additionally added.

Formulations of suitable cosmetic compositions may be provided in, for example, solutions, gels, solids or kneaded dry products; emulsions, suspensions, microemulsions, microcapsules, microgranules or ionic (liposomes) obtained by dispersing the oil phase in an aqueous phase; the form of a non-ionic vesicular dispersant, cream, skin, lotion, powder, ointment, spray or the form of a cone stick. In addition, it may be prepared in the form of a foam or an aerosol composition further containing a compressed propellant. Products to which the cosmetic composition of the present invention can be added include, but are not limited to, formulations such as skin lotions, skin softener, skin toner, astringent lotion, softening lotion, nourishing lotion, astringent, lotion, milk lotion, moisture lotion, nourishing lotion, body cream, massage cream, nourishing cream, moisture cream, hand cream, essence, nourishing essence, pack, soap, shampoo, cleansing foam, cleansing lotion, cleansing cream, body lotion, body cleanser, treatment, essence, emulsion, press powder, loose powder, eye shadow and the like.

The present invention also provides a food composition for preventing or improving an inflammatory disease comprising the strain or a culture thereof as an active ingredient.

The composition for food according to the present invention includes all forms such as functional food, nutritional supplement, health food, health functional food and food additives and the like. The above types can be prepared in various forms according to conventional methods known in the art.

For example, as a health food, the composition for food of the present invention may be prepared in the form of tea, juice, and drink for drinking, or may be ingested by granulation, encapsulation, and powder. In addition, the composition for food of the present invention can be prepared in the form of a composition by mixing with known substances or active ingredients known to have an effect of protecting skin cells or improving wrinkles.

As the health food, it can be processed into, for example, leached tea, liquid tea, beverage, fermented milk, cheese, jelly, yogurt, juice, probiotic preparation and health supplement, etc. and it can be used in the form of various food additives according to other purposes. In addition, the formulation of health functional food may be in various forms such as solutions, emulsions, viscous mixtures, tablets, powders, pills, etc. and it can be administered by various methods such as simple drinking, injection, spray, or squeeze and the like.

Preferably, the food composition of the present invention has the advantage of having a more excellent effect by ingesting it in the form of inner beauty food. The inner beauty refers to a food that is called 'eating cosmetics or beauty food', and refers to a food that absorbs various ingredients good for the skin into the body and changes the skin constitution to be healthy, and just like choosing cosmetics for your skin type, you can choose and consume inner beauty food that suits your skin condition and lifestyle. More preferably, when a cosmetic containing the cosmetic composition and an inner beauty food containing the strain are mixed, the effect is significantly increased compared to using only cosmetics, which has the advantage of being able to see a more effective inflammatory disease improvement effect.

In addition, as a functional food, it can be prepared by adding the composition for food of the present invention to beverages (including alcoholic beverages), fruits and their processed foods (e.g., canned fruit, canned food, jam, marmalade, etc.), fish, meat and their processed foods (e.g., ham, sausage corn beef, etc.), breads and noodles (e.g., udon, soba, ramen, spaghetti, macaroni, etc.), fruit juice, various drinks, cookies, syrup, dairy products (e.g., butter, cheese, etc.), edible vegetable oil, margarine, vegetable protein, retort food, frozen food, various seasonings (e.g., miso, soy sauce, sauce, etc.) and the like. In order to use the composition for food of the present invention in the form of a food additive, it may be prepared and used in the form of a powder or a concentrate.

The content of the strain of the present invention as an active ingredient in the food composition according to the present invention is 0.01 to 99% by weight, preferably 0.1 to 50% by weight, more preferably 0.5 to 25% by weight, based on the total weight of the composition, but it is not limited.

In addition, in order to use the strain of the present invention in the form of a food additive, it may be prepared and used in the form of a powder or a concentrate.

In the pharmaceutical composition and food composition of the present invention, the mixing amount of the active ingredient may be suitably determined according to the purpose of its use (prevention, health or symptom relief), but it is not limited thereto, for example, it may include the strain according to the present invention at a concentration of $10^8$ CFU/g to $10^{20}$ CFU/g. The effective dose of the strain of the present invention can be used according to the above concentration range, but in the case of long-term ingestion for health and hygiene purposes or for health control, it may be less than the above range, and it can be used in an amount beyond the above range since the active ingredient has no problem in terms of safety.

In addition, the present invention provides a probiotic or enteral composition comprising the strain or a culture thereof as an active ingredient.

The novel strain according to the present invention can be used as a probiotic composition for enteral probiotics for promoting human and animal health or a probiotic composition for feed for animals. The composition includes the strain itself, or a culture thereof as an active ingredient, and may further include an excipient or carrier. The content of the novel strain of the present invention in the composition may vary depending on the use and formulation of the composition.

The enteral or probiotic composition according to the present invention can be prepared and administered in various formulations and methods. For example, the novel strain or culture thereof according to the present invention may be prepared and administered in the form of a tablet, troche, capsule, elixir, syrup, powder, suspension or granule and the like by mixing it with a carrier and flavoring commonly used in the pharmaceutical field. As the carrier, binders, lubricants, disintegrants, excipients, solubilizers, dispersants, stabilizers, suspending agents, and the like can be used.

The administration method may be oral, parenteral or application method and the like. In addition, the dosage can be appropriately selected according to the absorption of the active ingredient in the body, the inactivation rate and excretion rate, the age, sex, condition of the subject, and the like.

In addition, the novel strain or culture thereof according to the present invention can be used as a food additive for foods such as kimchi, beverages, and baby food, in particular, as a starter for the production of fermented products. The 'fermented product' may be used interchangeably with the term 'fermented food' in this specification. The fermented product is not limited in its kind as long as it is known in the art as a food that requires a fermentation process during manufacture, for example, it includes cheese, yogurt, butter, cream, ice cream, lactic acid bacteria beverage, kefir, fermented milk, kimchi, fermented raw products, and the like. The fermented product using the novel strain of the present invention can be prepared according to a conventional method known in the art. The manufacturing method of a fermented product usually consists of processes such as preparation of raw materials, addition of lactic acid bacteria, fermentation, and recovery of the finished product, and the like. The preparation step of the raw material is a step of preparing the material to be fermented and preparing the fermentation conditions so that the fermentation takes place well. The addition of lactic acid bacteria is to add an appropriate amount of bacteria according to the amount of fermentation target. Fermentation is carried out according to the fermentation conditions of conventional fermenting bacteria, and may be performed, for example, at 20° C. to 40° C. for 1 to 168 hours. The recovery of the finished product includes all post-processing processes and packaging for facilitating storage and transportation, from removing unnecessary by-products or unfermented materials from the fermented product.

In addition, the present invention provides an immunomodulatory composition comprising the strain or a culture thereof as an active ingredient.

"Cells" involved in immunomodulation composed of Th1 cells that produce interleukin-2 (IL-2), interferon γ (IFN-γ), and TNF-α, etc. and Th2 cells that produce IL-4, IL-5, IL-6, IL-10, and IL-13 etc. Immune balance regulated by cytokines produced by these Th1 and Th2 cells is called Th1/Th2 balance, there are known that Th1 cells are important for the regulation of cellular immunity, and Th2 cells play an important role in the regulation of humoral immunity. In the steady state, cytokines centered on IFN-γ, which are important for Th1 differentiation, and cytokines, mainly with IL-4, which are important for Th2 differentiation, interfere with each other, maintaining a constant Th1/Th2 balance. However, if the Th1/Th2 balance is disturbed, it can cause various immune diseases, in case of bias to Th1, cellular immunity is revived and infection resistance is enhanced and in the case of Th2 bias, infection resistance decreases, and conversely, allergy increases.

In addition, the yeast according to the present invention has physiological activity that regulates the balance of Th1/Th2 immune response by inhibiting Th2 cytokines (e.g., IL-4, IL-5) and/or inducing Th1 cytokines (e.g., IL-12, IFN-γ, TNF-α). Specific physiological activities are as follows. 1) increase the production of IL-12, IFN-γ, TNF-α in ovalbumin-sensitized mice; 2) reduces IgE levels in mouse serum. 3) reduce the ratio of eosinophils, neutrophils and basophils. 4) inhibits the expression of cytokines (IL-4 and IL-10) mediated by Th2-lymphocytes; 5) reduces eosinophil and mast cell infiltration in atopic dermatitis lesions.

In addition, the present invention provides a food additive composition comprising the strain or a culture thereof as an active ingredient.

The strain of the present invention or a culture thereof according to the present invention may be used as a food additive for foods such as kimchi, beverages, baby food, fermented milk, and bread. In addition, the strain of the present invention or a culture thereof can be used as a starter for producing a fermented product. The fermented products include cheese, kimchi, fermented raw products, and the like. Fermented products using the strain of the present invention or a culture thereof can be prepared according to a conventional method known in the art. For example, after fermentation at an appropriate temperature by treating the strain according to the present invention or two or more types of mixed lactic acid bacteria containing the same to grain powder such as brown rice and barley radish, then fermented raw products may be manufactured by properly blending a variety of agricultural products such as white rice, glutinous rice, and sorghum to ensure excellent nutritional balance and palatability.

The present invention provides use of the strain or a culture thereof for preparing an agent for the prevention or treatment of inflammatory diseases.

The present invention provides a method for treating an inflammatory disease comprising administering to a subject in need thereof an effective amount of a composition comprising the strain or a culture thereof as an active ingredient.

The present invention provides use of the strain or a culture thereof for the production of a probiotic agent.

The present invention provides use of the strain or a culture thereof for preparing an enteral agent.

The present invention provides use of the strain or a culture thereof for preparing an immunomodulatory agent.

The present invention provides a method of immunomodulation comprising administering to a subject in need thereof an effective amount of a composition comprising the strain or a culture thereof as an active ingredient.

The present invention provides use of the strain or a culture thereof for preparing a food additive agent.

The 'effective amount' of the present invention refers to an amount that, when administered to a subject, has an effect of improving, treating, preventing, detecting, diagnosing, or inhibiting or reducing an inflammatory disease, and the 'subject' may be an animal, preferably an animal, including a mammal, particularly a human, and may be an animal-derived cell, tissue, organ, or the like. The subject may be a patient in need of the effect.

The 'treatment' of the present invention refers to improving inflammatory diseases or symptoms of inflammatory diseases comprehensively, and this may include curing, substantially preventing, or ameliorating the condition of the diseases, and include alleviating, curing or preventing one or most of the symptoms resulting from the disease, but it is not limited thereto.

Advantageous Effect

The novel yeast according to the present invention has anti-inflammatory activity by promoting Treg-mediated Th2 immune response, and has intestinal effect, and is excellent for the effect of inhibiting inflammation in the skin and intestines in the ovalbumin-sensitized mouse model. In addition, it has excellent acid resistance and bile resistance, and thus has high commercial use value.

BRIEF DESCRIPTION OF THE DRAWINGS

FIG. 3A is a result confirming the effect on the IL-4 concentration.

FIG. 3B is a result confirming the effect on the IL-5 concentration.

FIG. 3C is a result confirming the effect on the IL-10 concentration.

FIG. 3D is a result confirming the effect on the IL-12 concentration.

FIG. 3E is a result confirming the effect on the IFN-γ concentration.

FIG. 3F is a result confirming the effect on the TNF-α concentration.

FIG. 3G is a result confirming the effect on the IL-1β concentration.

FIG. 4A is a result of measuring the IgE level in serum by ELISA analysis to confirm an allergic reaction.

FIG. 4B is the result of confirming the eosinophil ratio.

FIG. 4C is a result of confirming the number of eosinophils.

FIG. 4D is the result of confirming the neutrophil ratio.

FIG. 4E is a result of confirming the basophil ratio.

FIG. 5A is the result of measuring the Shannon-wiener index (defined as 97% similarity).

FIG. 5B is a result of measuring the Simpson index.

FIG. 5C is a result of estimating the difference in the intestinal microbial group with an Unweighted UniFrac-based (PCoA) 3D diagram (Blue label: negative control group; Red label: positive control group; Green label: *K. turicensis* CAU Y1706 administration group; Purple label: Betotastine besilate administration group).

FIG. 5D is a result showing the relative abundance ratio of units of the genus.

FIG. 5E is a result showing a scatter plot of *Faecalibacterium*.

FIG. 5F is a result showing a scatter plot of the genus *Akkermansia*.

FIG. 5G is a result showing a scatter plot of the genus *Lactobacillus*.

FIG. 5H is a result showing a scatter plot of the genus *Ruminococcus*.

A statistical difference was revealed by the nonparametric Kruskal-Wallis test in the comparison of the four groups of FIGS. 5*e* to 5*h* ($p<0.05$).

FIGS. 6A to 6D are results confirming the effect of oral administration of *Kazachstania turicensis* CAU Y1706 on atopic dermatitis skin lesions in mice.

Significance indicates the difference between the ANOVA analysis value and the mean value of the positive group. $*p<0.05$; $p<0.005$; $*p<0.0005$; $****p<0.0001$.

Figure 6A:
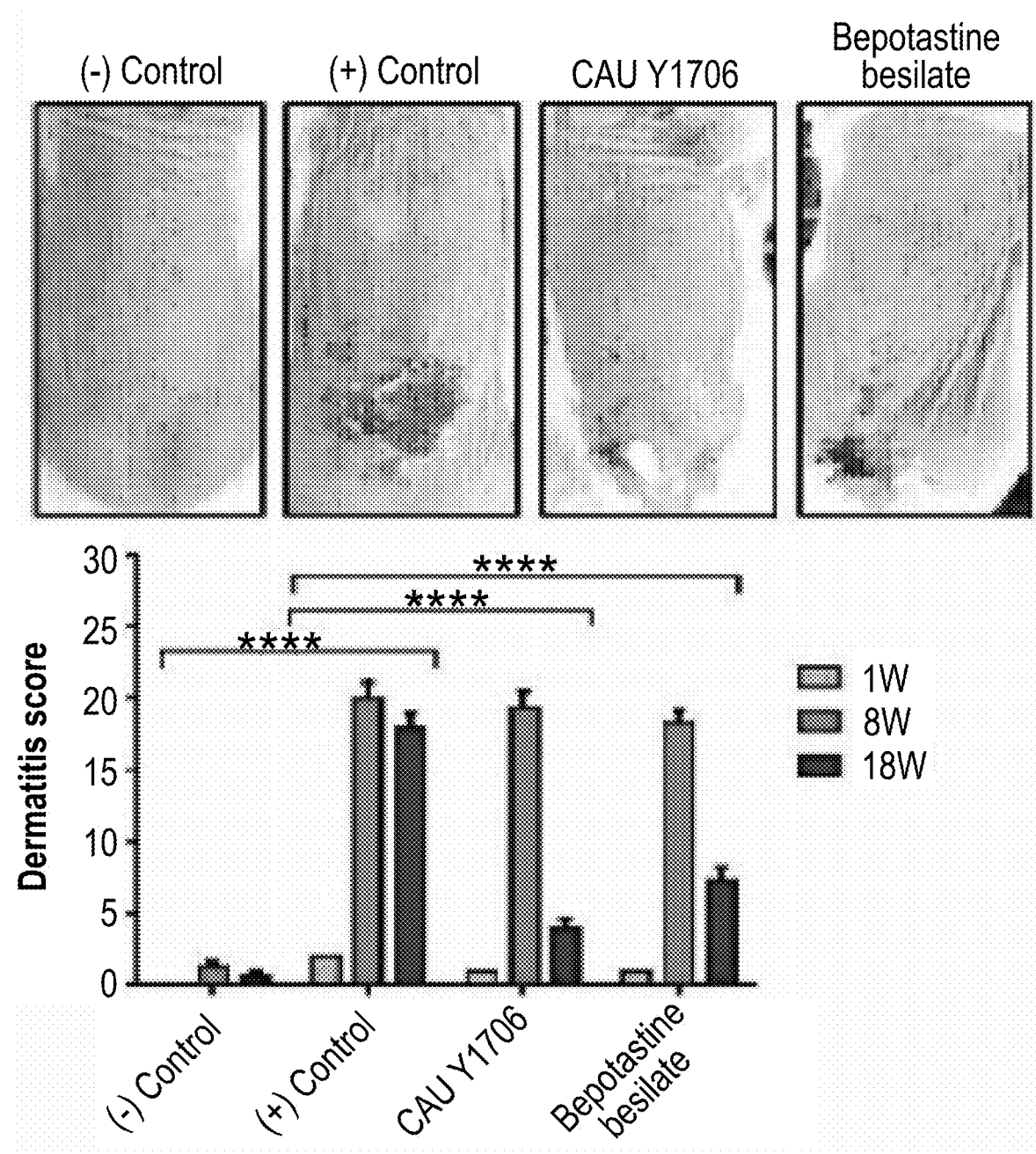

FIG. 6A shows that atopic lesions of the skin such as a mouse were evaluated as a dermatitis index, and the dermatitis score was calculated as the sum of the scores of three symptoms: erythema, dryness, and scratching by the rat.

Figure 6B:
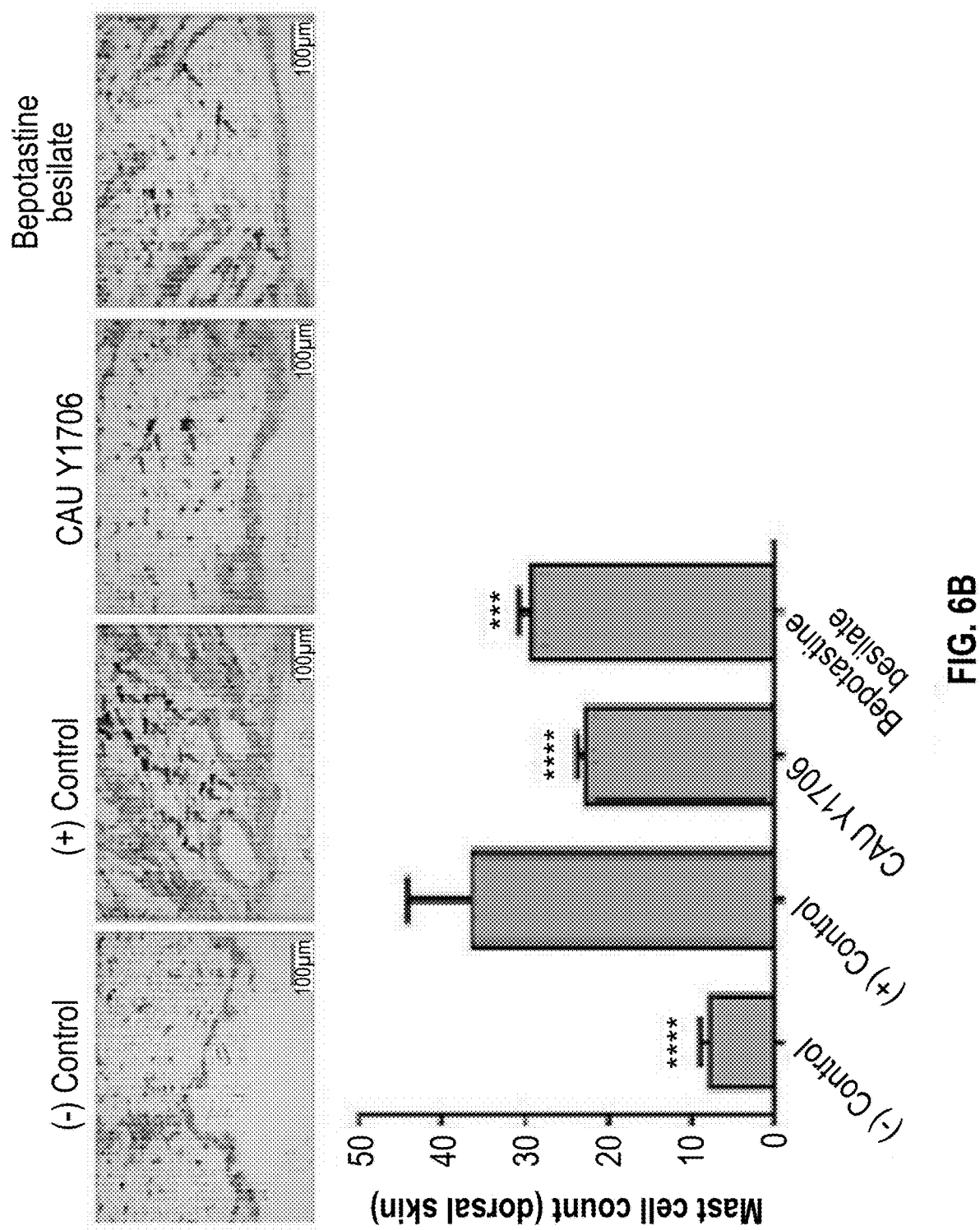

FIG. 6B is the result of measuring the number of mast cells using a microscope by staining the paraffin block of mouse back skin with toluidine blue (scale bar=100 μm).

Figure 6C:
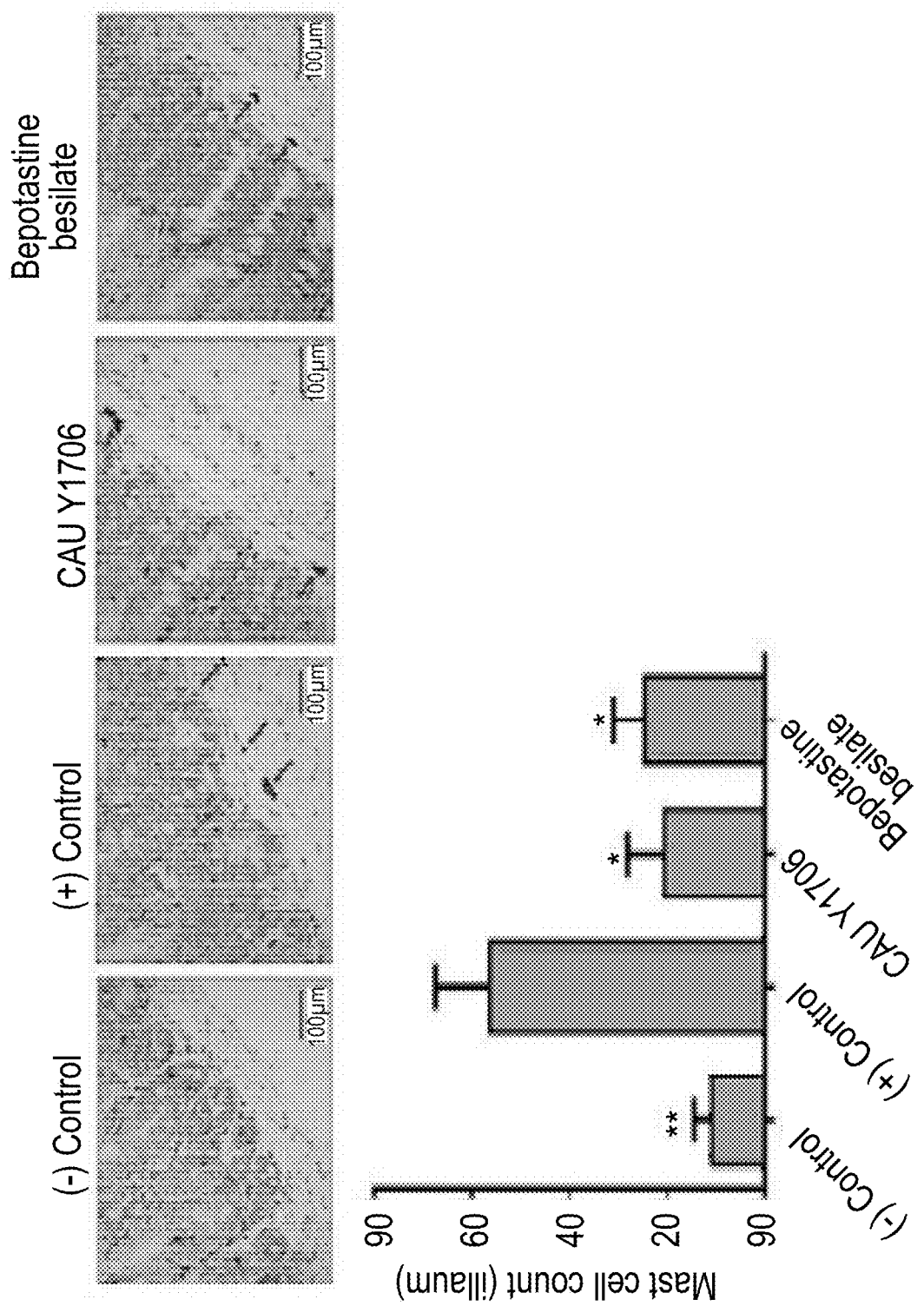

FIG. 6C is the result of measuring the number of mast cells using a microscope by staining the paraffin block of the mouse ileum with toluidine blue (scale bar=100 μm).

Figure 6D:
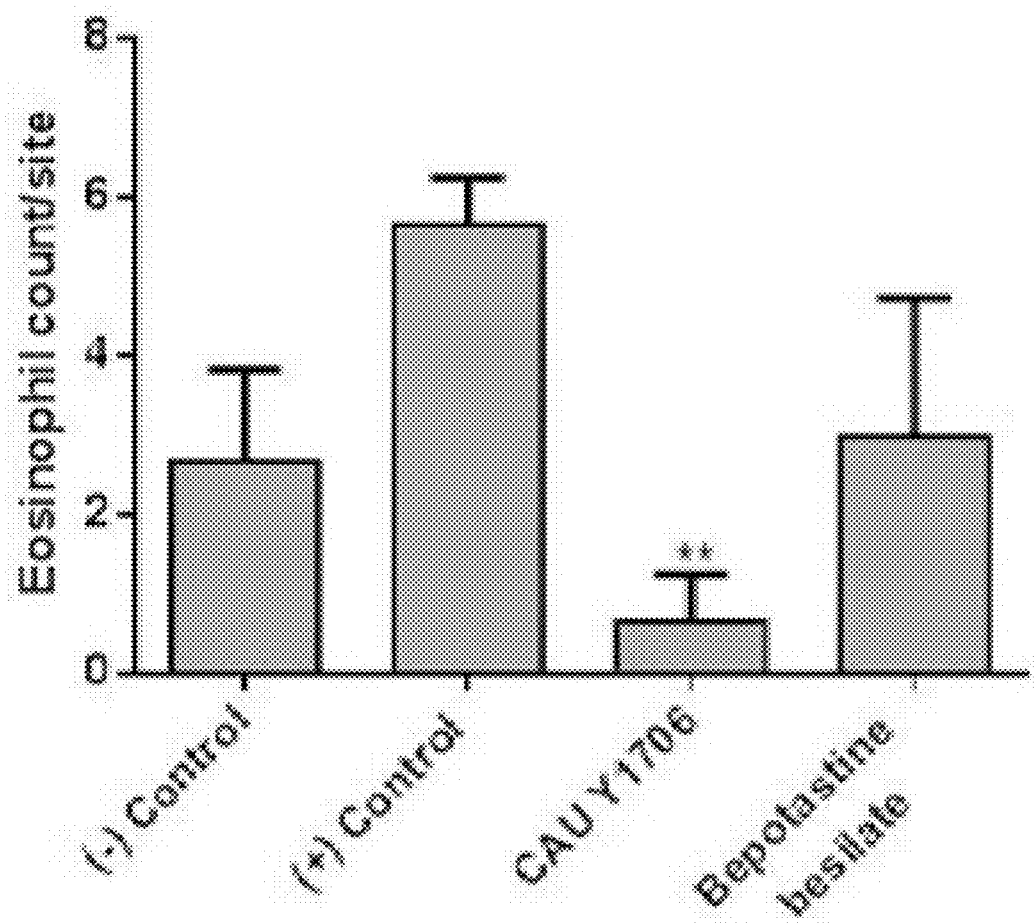

FIG. 6D is a result of quantifying the number of eosinophils through microscopic analysis after staining mouse back skin tissue with Congo red.

MODE FOR CARRYING OUT INVENTION

Hereinafter, the present invention will be described in detail.

However, the following examples only illustrate the present invention, and the content of the present invention is not limited to the following examples.

EXPERIMENTAL MATERIALS AND METHODS

Isolation and identification of *Kazachstania turicensis* CAU Y1706 Kimchi samples were obtained from a traditional market in Seoul, Korea. All samples were chopped and mixed with 10 mL of peptone solution (0.85% mass/vol). After serial dilution, samples were plated on MRS (Man, Rogosa, and Sharpe; BD BBL, Spatks, MD. USA) solid medium, and was cultured for 2-3 days in a MIR-254-PK incubator (Panasonic, Osaka, Japan) at 30° C. For pure isolation, white colonies were selected and separated and cultured several times on a soybean casein digested agar medium (Tryptic Soy Agar-TSA; BD BBL), and all separations were performed at 30° C. for 24 hours. For isolation and identification of yeast, rRNA gene (18S, 26S, 5.8-ITS) sequencing method was used, and a 3730 automatic DNA sequencer (Applied Biosystems, Foster City, CA, USA) was used for the analysis. The gene sequence was analyzed through NCBI BLAST (https://blast.ncbi.nlm.nih.gov/Blast.cgi). After the selected yeast is cultured in TSA at 30° C., cell appearance was observed using an optical microscope, DM 1000 light (Leica, Wetzlar, Germany) and a scanning electron microscope, SIGMA field-emission scanning electron microscope (Carl Zeiss, Dresden, Germany).

Biochemical properties were confirmed using API 20C AUX and API 50CH, and performed according to the MANUFACTURER'S INSTRUCTIONS (BIOMERIEUX, MARCY-I'É TOILE, FRANCE). ONE OF THE ISOLATES, *K. turicensis* CAU Y1706, was used in the study of atopic dermatitis.

The *Kazachstania turicensis* strain selected in this way was named CAU Y1706. The novel *Kazachstania turicensis* strain isolated and identified was deposited at the Korea Research Institute of Bioscience and Biotechnology Biological Resources Center (KCTC) on Jan. 22, 2019 (Accession number: KCTC13794BP).

Ethics and Experimental Design

Figure 1:
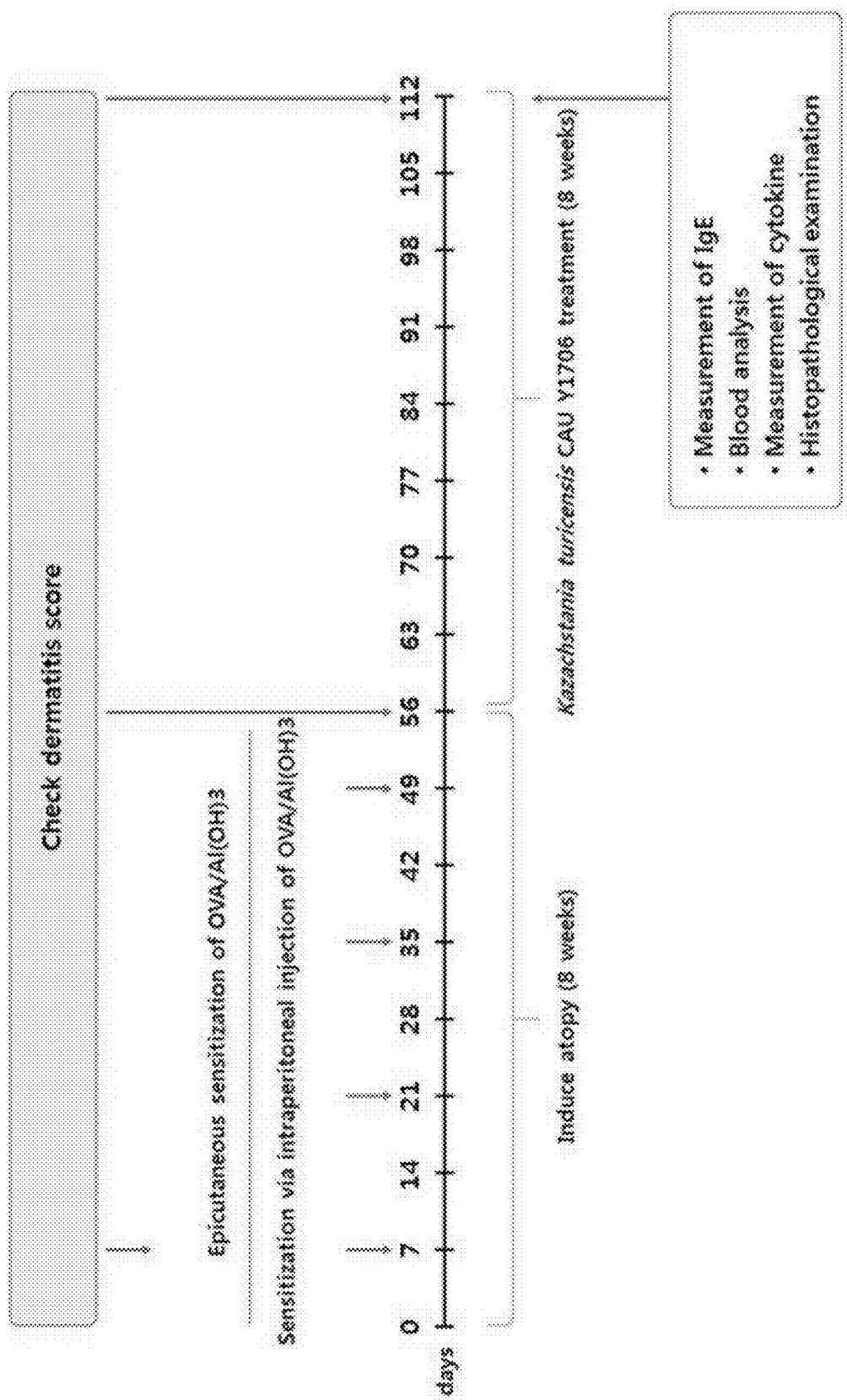
FIG. 1 is a diagram showing the experimental design and schedule of atopic dermatitis induction in OVA-sensitized mice for the experiment.

Animal experiments were conducted in accordance with the guidelines of the Korea Food and Drug Administration. The rat blood and tissue samples were collected according to the guidelines of the Animal Bioethics Committee of Chung-Ang University. Five-week-old female BALB/c rats (40 rats) were sold from Central Experimental Animals (Seoul, Korea). The experimental design and schedule are shown in FIG. 1. All mice were randomly assigned to 4 groups of 10 each, negative control group (negative control, OVA non-sensitized+PBS), positive control group (positive control, OVA sensitized+PBS), *K. turicensis* CAU Y1706 group (OVA sensitized+*K. turicensis* CAU Y1706), bepotastine besilate group (OVA sensitization+bepotastine besilate). To induce atopic dermatitis through skin sensitization, all mice were depilated with a hair clipper and depilatory cream. An aqueous solution of OVA grade V (Sigma-Aldrich, St. Louis, MI, USA) (50 mg/mL) and alum (Sigma-Aldrich) dissolved in phosphate buffered saline (PBS) was injected intraperitoneally on the 7th, 21st, 35th, and 49th days from the start of the experiment, and according to the procedure, the skin was directly sensitized for 8 weeks. Lyophilized *K. turicensis* CAU Y1706 ($1\times10^{10}$ CFU/mouse) was dissolved in 200 µl of phosphate buffered saline and then orally administered. The negative control group was administered the same dose of phosphate buffered saline for 8 weeks. Bepotastine besilate (Sigma-Aldrich) in the positive treatment control group was orally administered once a day (0.5 mg/kg). After 8 weeks, mice were sacrificed for analysis, and back skin, ileum, and blood were collected.

Blood and Serum Cytokine Analysis

Blood samples were obtained through orbital blood sampling using a capillary. Whole blood for eosinophil analysis and number confirmation was collected using an EDTA blood collection tube (Green Cross Laboratories, Yongin, Korea). Serum for IgE and cytokine (IL-4, IL-5, IL-10, IL-12, IL-1β, TNF-α, IFN-γ) analysis was coagulated at 4° C. for 1 hour and then was obtained after the thrombus was settled through a 5,000×g centrifugation process. Cytokines were identified using an ELISA kit, and was performed according to the manufacturer's instructions (R&D systems, Minneapolis, MN. USA). To check the absorbance at 450 nm, an Infinite 200 PRO NanoQuant microplate reader (Tecan, Mannedorf, Switzerland) was used.

Gut Microbiome Analysis

The fecal sample collected from 16-week-old mice was placed in a sterile 2 mL tube and immediately stored on ice, and then stored at −80° C. DNA was extracted using FastDNA SPIN kit for bacterial DNA, and performed according to the manufacturer's instructions (MP Biomedicals, Santa Ana, CA, USA). The V3-V4 region of the 16S rRNA gene was amplified through PCR, and analysis was performed by MiSeq-based high-throughput sequencing (Illumina, San Diego, CA, USA). After sequencing, the adapter sequence was removed through the Scythe (v 0.994; https://github.com/vsbuffalo/scythe) and Sickle programs (https://github.com/vsbuffalo/scythe). Sequences that are too short (<36 bp), extra-long tails, chimeric reads, and noise sequences were cut out using CD-HIT-OTU (http://weizhong-lab.ucsd.edu/cd-hit-otu). (Li et al., 2012). Minimum quality scores and length were limited to >20, 300 bp, respectively. The remaining representative sequences were combined, and operational taxonomic units were defined with 97% similarity through CD-HIT-OTU. Intestinal microbiome analysis was performed using QIIME (Quantitative Insight Into Microbial Ecology; v.1.9.1) software.

Tissue Analysis

The skin tissue and ileum of the back of the sacrificed mice were used for tissue analysis. The tissue was fixed in a formalin solution diluted to 10% using phosphate buffered saline and then embedded in paraffin. Tissue samples were cut to a thickness of 4-5 µm using a microtome, and then were stained with hematoxylin, eosin, toluidine blue and Congo red, respectively, for the measurement of mast cells and eosinophils. All toluidine blue stained areas of ileal tissue samples for mast cell count were observed at 400 times magnification by DM 4000B microscopy. For the quantification of mast cells, 5 of the toluidine blue stained areas of the skin tissue of the back were randomly selected, and for the quantification of eosinophils, 20 of Congo red stained areas were randomly selected.

Statistics

GraphPad Prism (v.7.0) software was used for statistical analysis, and the data were expressed as mean±standard error. Comparisons between groups to identify relative differences in microbial classes and genera were based on statistically significant differences by nonparametric Kruskal-Wallis test. Significant differences in cytokine, blood sample, and tissue analysis were calculated by ANOVA analysis to compare two or more groups, and if the p value was less than 0.05, it was considered as significant.

Example 1: Isolation of *Kazachstania turicensis* CAU Y1706

Figure 2:
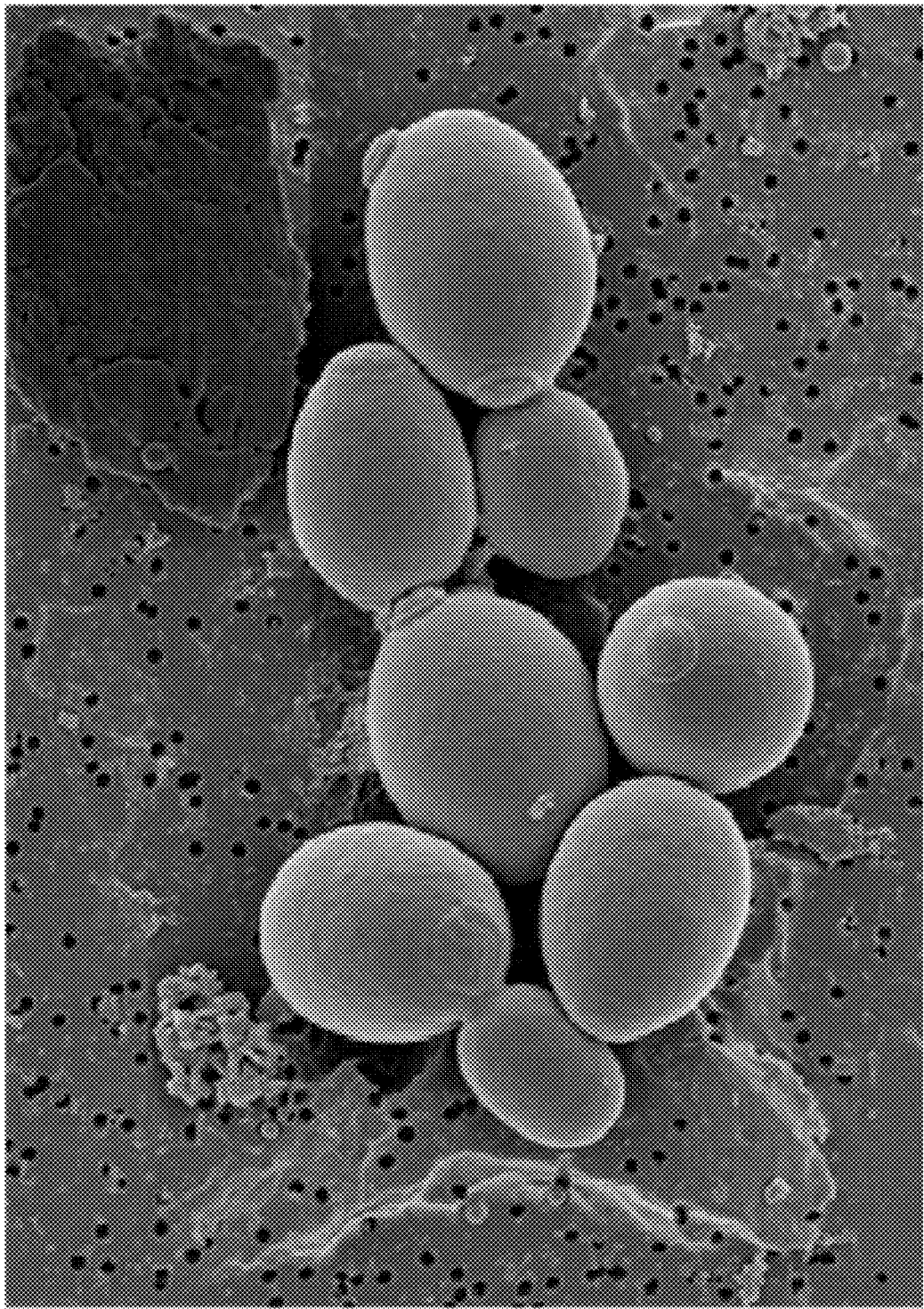
FIG. 2 is a scanning electron microscope (SEM) photograph of *Kazachstania turicensis* CAU Y1706.

*K. turicensis* CAU Y1706 was cultured for one day in TSA medium (Bacto) in an environment of 30° C. to form round glossy cream-colored colonies. Cells were observed to be ellipsoidal, about 1.6-2.3 µm in diameter and 1.6-2.3 µm in length (FIG. 2). It was confirmed that *K. turicensis* CAU Y1706 can utilize D-glucose, D-galactose, D-saccharose, D-trehalose, D-raffinose, D-fructose, D-mannose, 2-keto-D-gluconate as a carbon source. On the other hand, it was found that glycerol, L-arabinose, D-xylose, adonitol, xylitol, inositol, D-sorbitol, alpha-methyl-D-glucoside, N-acetyl-D-glucosamine, D-cellobiose, D-lactose, D-maltose, D-melezitose, D-ribose, D-mannitol, D-turanose and D-lyxose could not be used as carbon sources. After 100 µl treatment and reaction for 1 hour, absorbance was measured at 450 nm.

Example 2: Effects of *Kazachstania Turicensis* CAU Y1706 on Cytokine Levels

Figure 3A:
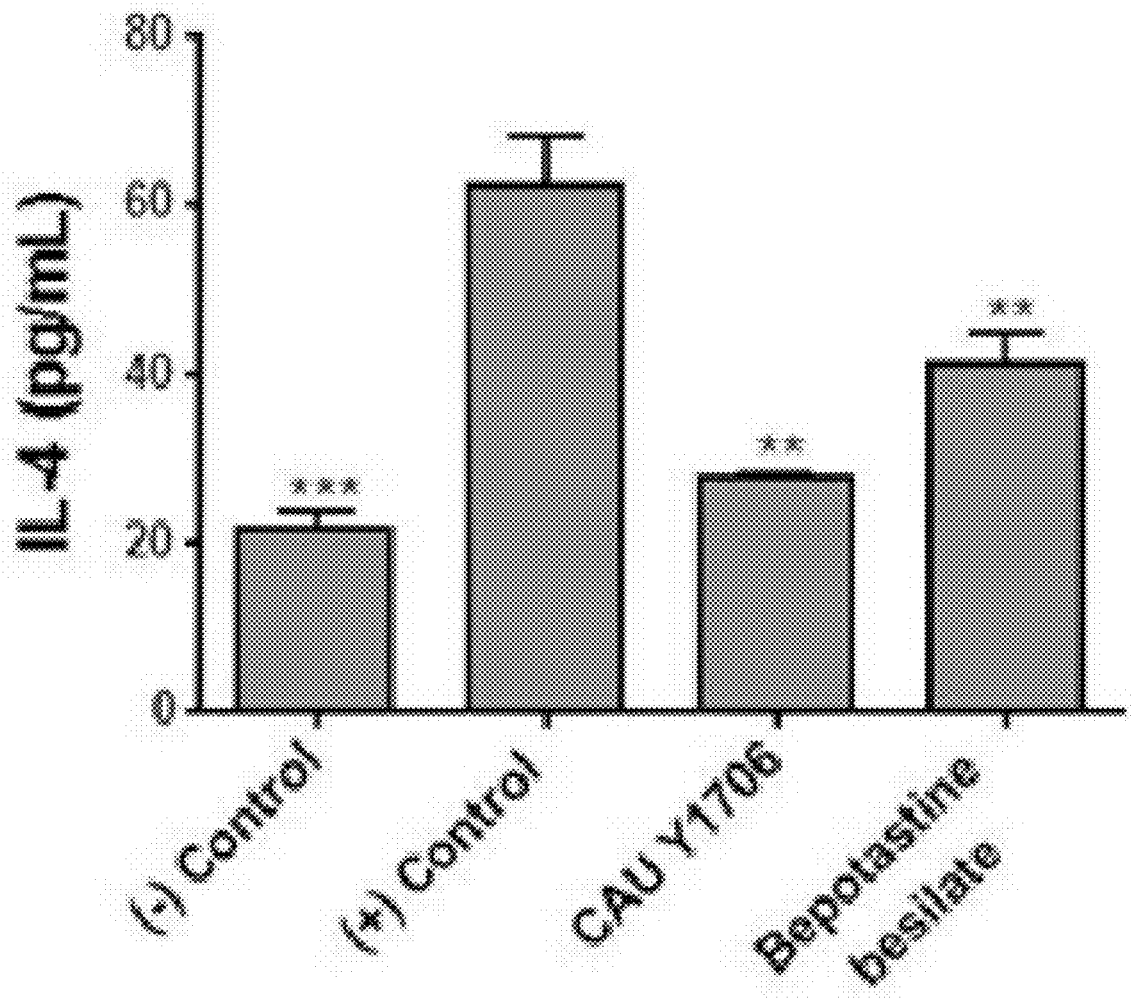
FIGS. 3A to 3G are results confirming the effect of oral administration of *Kazachstania turicensis* CAU Y1706 on cytokine concentration. Serum was used to analyze the level, and the ELIZA kit was used. Significance indicates the difference between the ANOVA analysis value and the mean value of the positive group. $*p<0.05$; $p<0.005$; $*p<0.0005$; $****p<0.0001$.
Figure 3B:
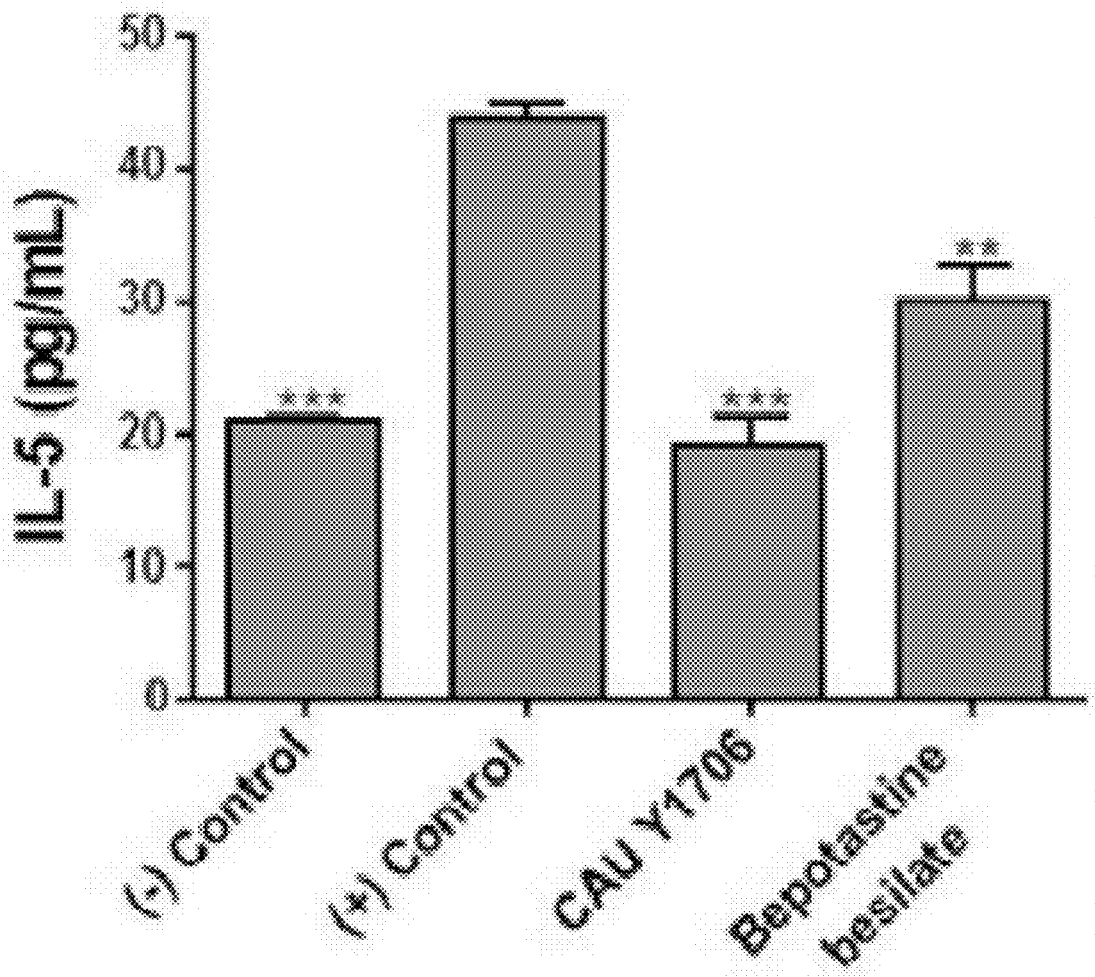
Figure 3C:
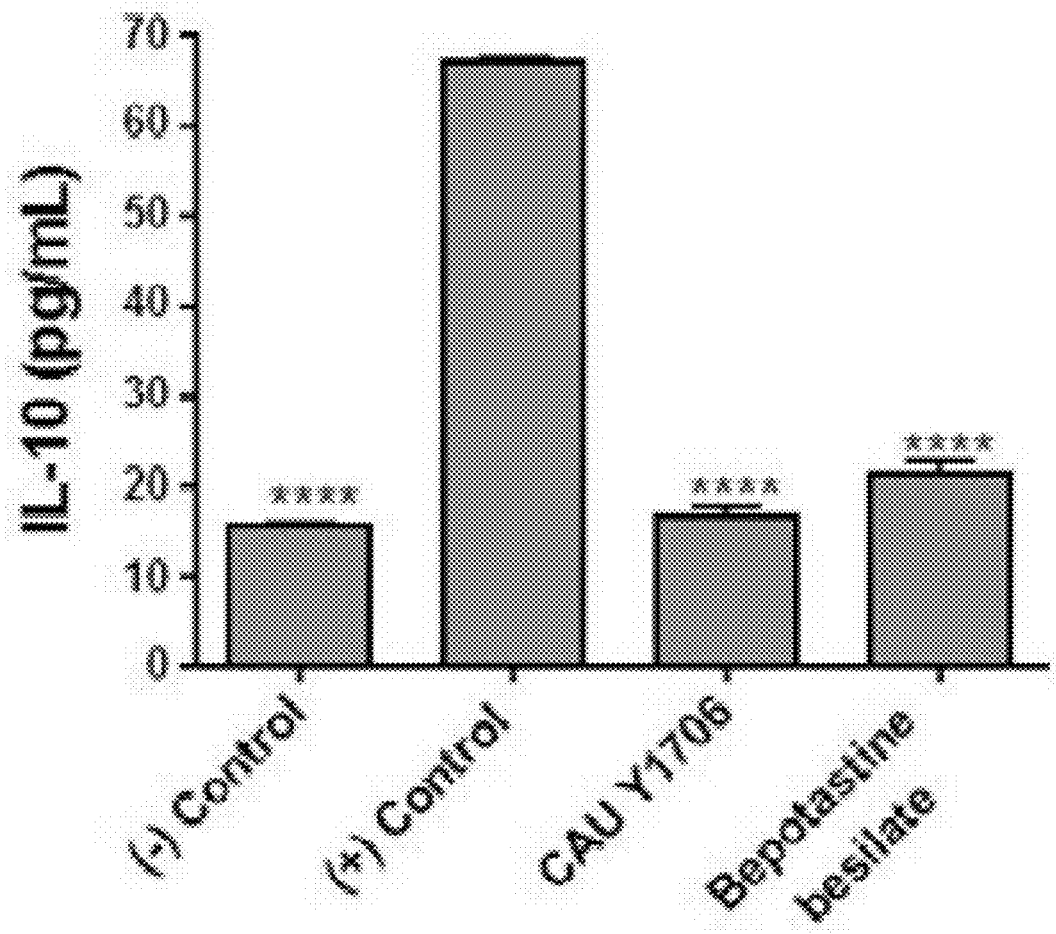

The effect of *K. turicensis* CAU Y1706 on serum cytokine production was examined. When compared with the positive control group, the concentration of Th2 cytokines such as IL-4 and IL-5 in the serum of the *K. turicensis* CAU Y1706 administration group was significantly lower. Bepotastine besilate administered group also showed a low level (FIGS. 3a and 3b). Compared with the positive control group, Treg cytokine levels such as IL-10 and IL-1β3 in the serum were also lower in the *K. turicensis* CAU Y1706 administration group (FIGS. 3c and 3g).

Figure 3D:
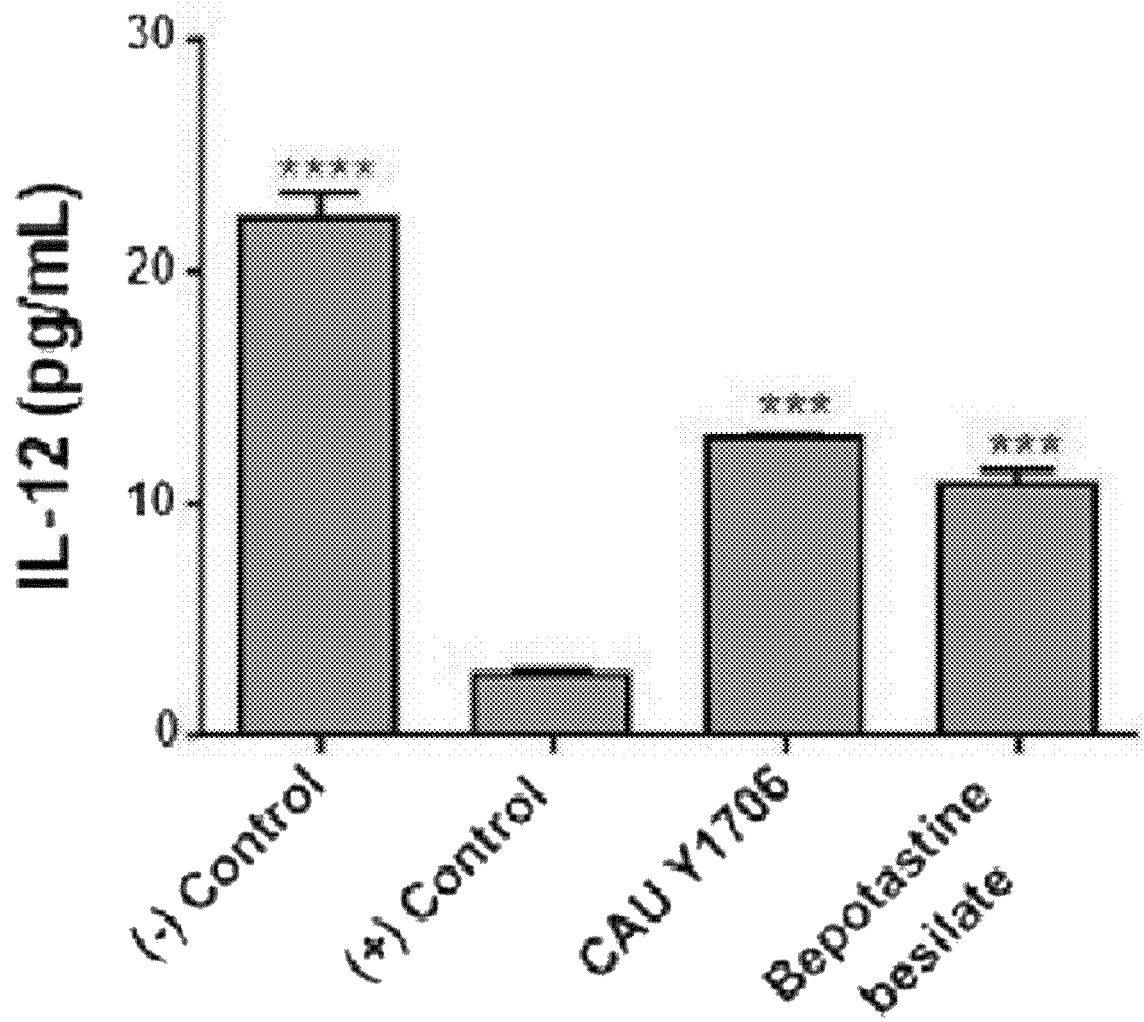
Figure 3E:
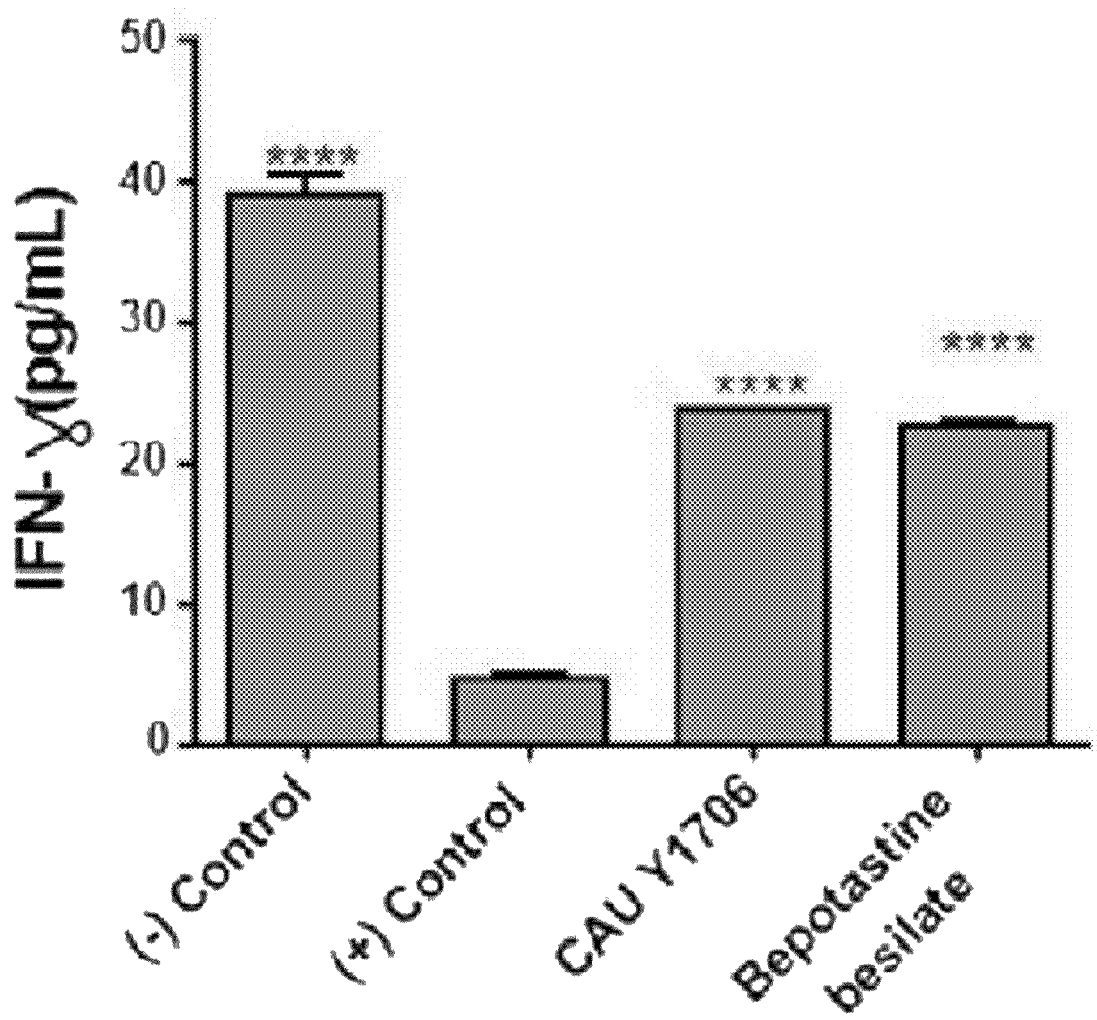
Figure 3F:
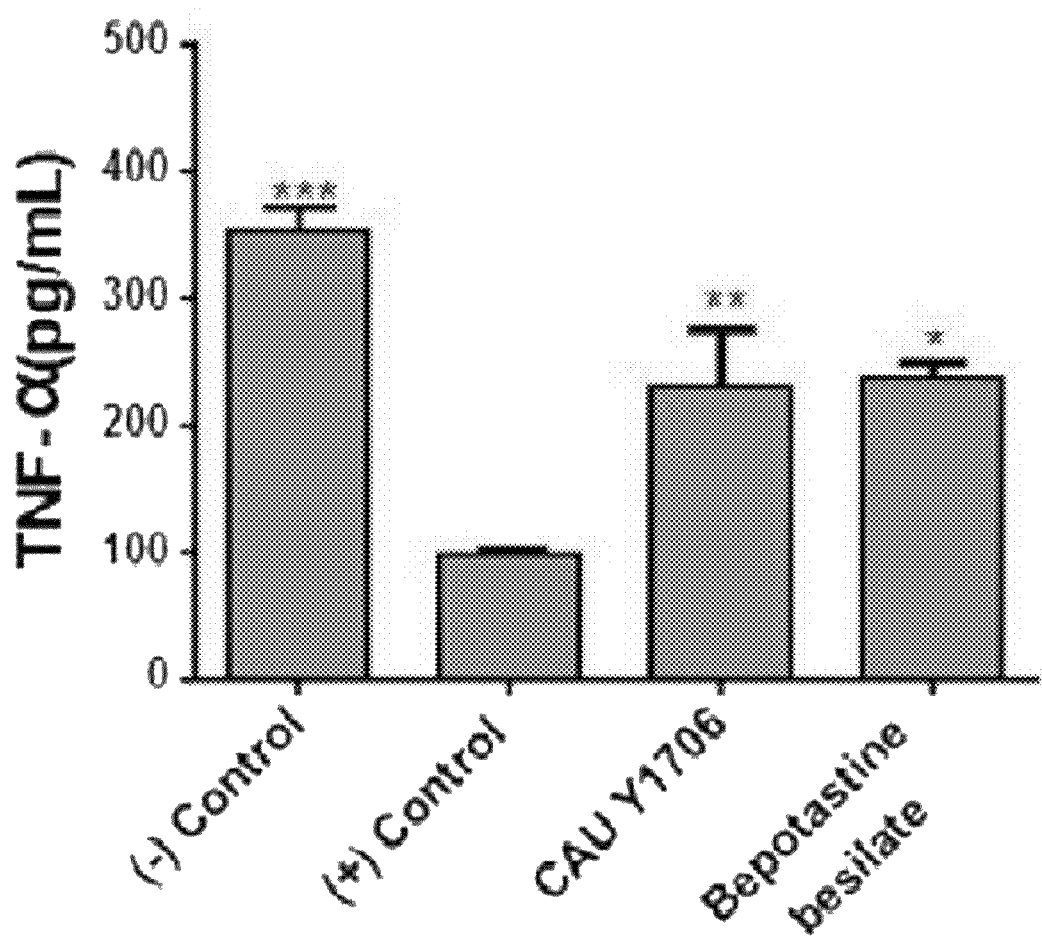
Figure 3G:
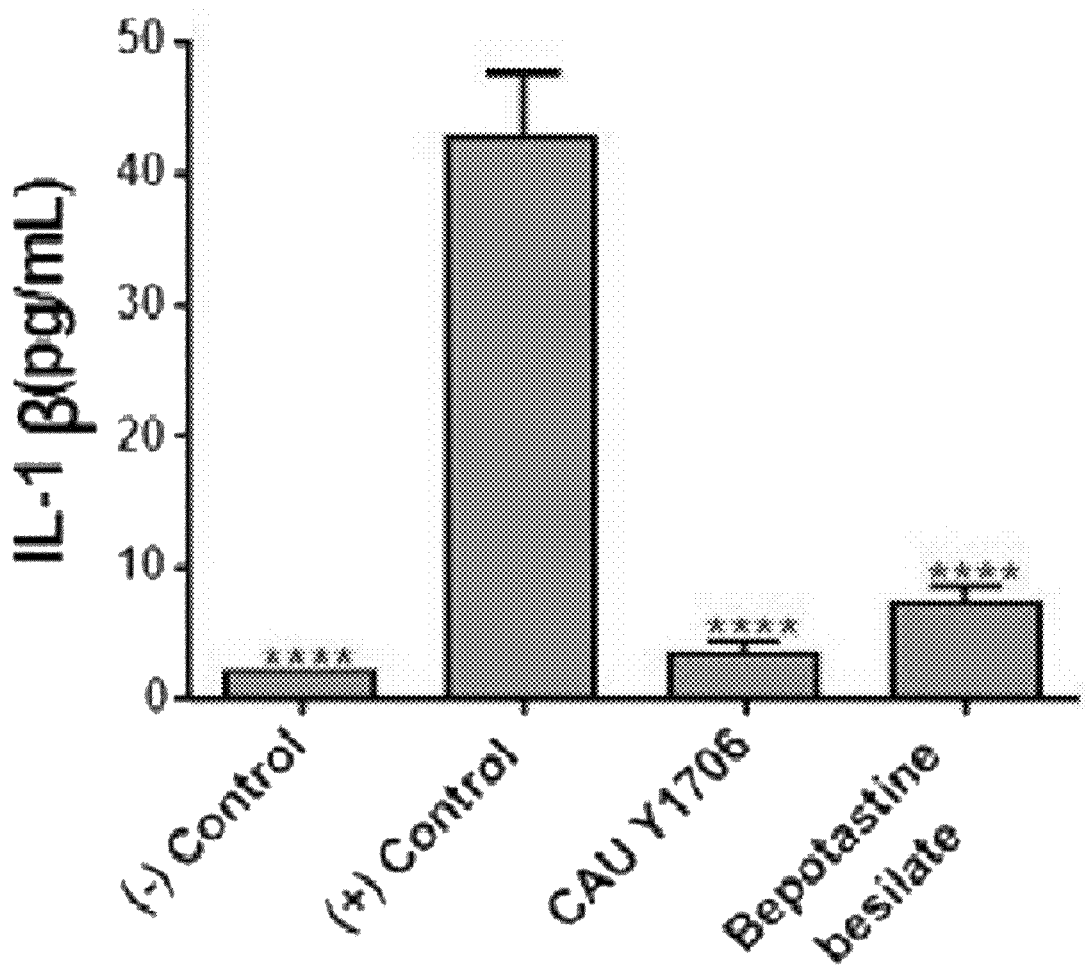

On the other hand, it was confirmed that the level of Th1 cytokines such as IFN-γ, TNF-α, IL-12 was higher in the *K. turicensis* CAU Y1706 administration group compared to the positive control group (FIGS. 3d to 3f). These results support the therapeutic effect of *K. turicensis* CAU Y1706 on inflammatory diseases by promoting Treg-mediated Th2 immune response.

In addition, it was confirmed that the group treated with the strain of the present invention was significantly superior in IFN-γ, TNF-α, IL-12 production compared to the control group.

Figure 4A:
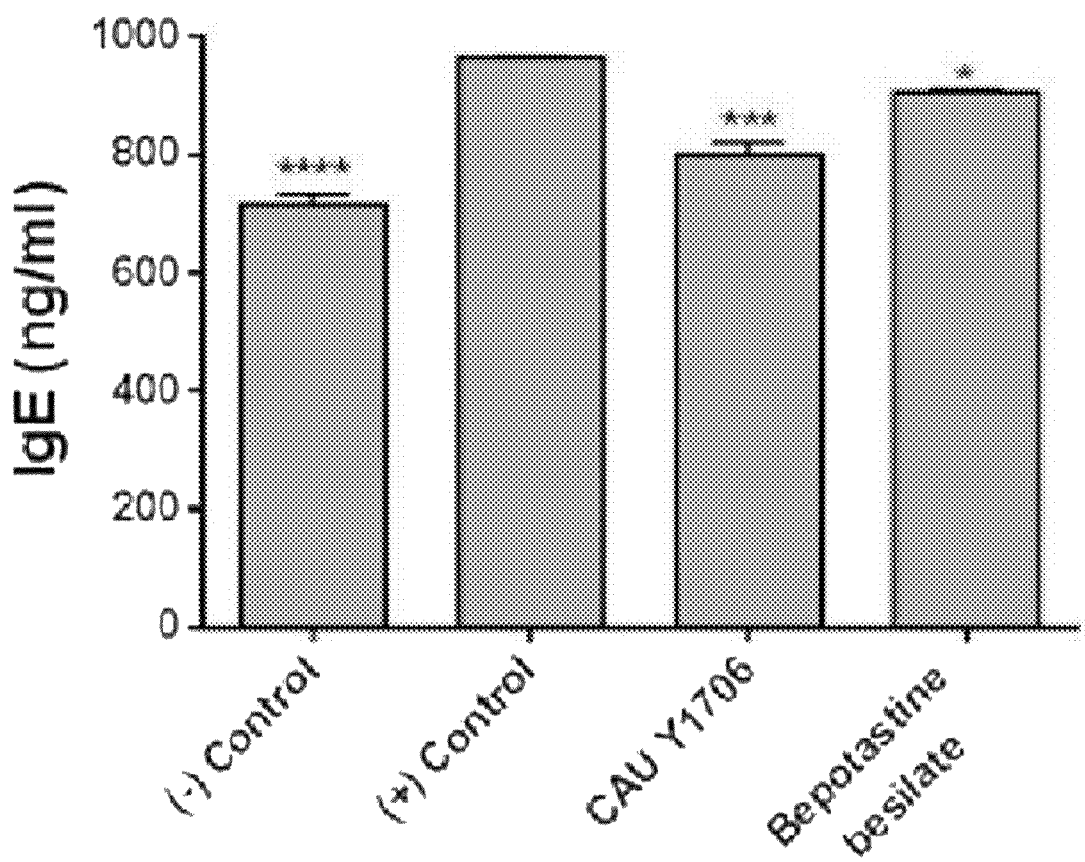
FIGS. 4A to 4E are results of confirming the effect of oral administration of *Kazachstania turicensis* CAU Y1706 on blood. Inflammation was confirmed by whole blood analysis. Significance indicates the difference between the ANOVA analysis value and the mean value of the positive group. $*p<0.05$; $p<0.005$; $*p<0.0005$; $****p<0.0001$.
Figure 4B:
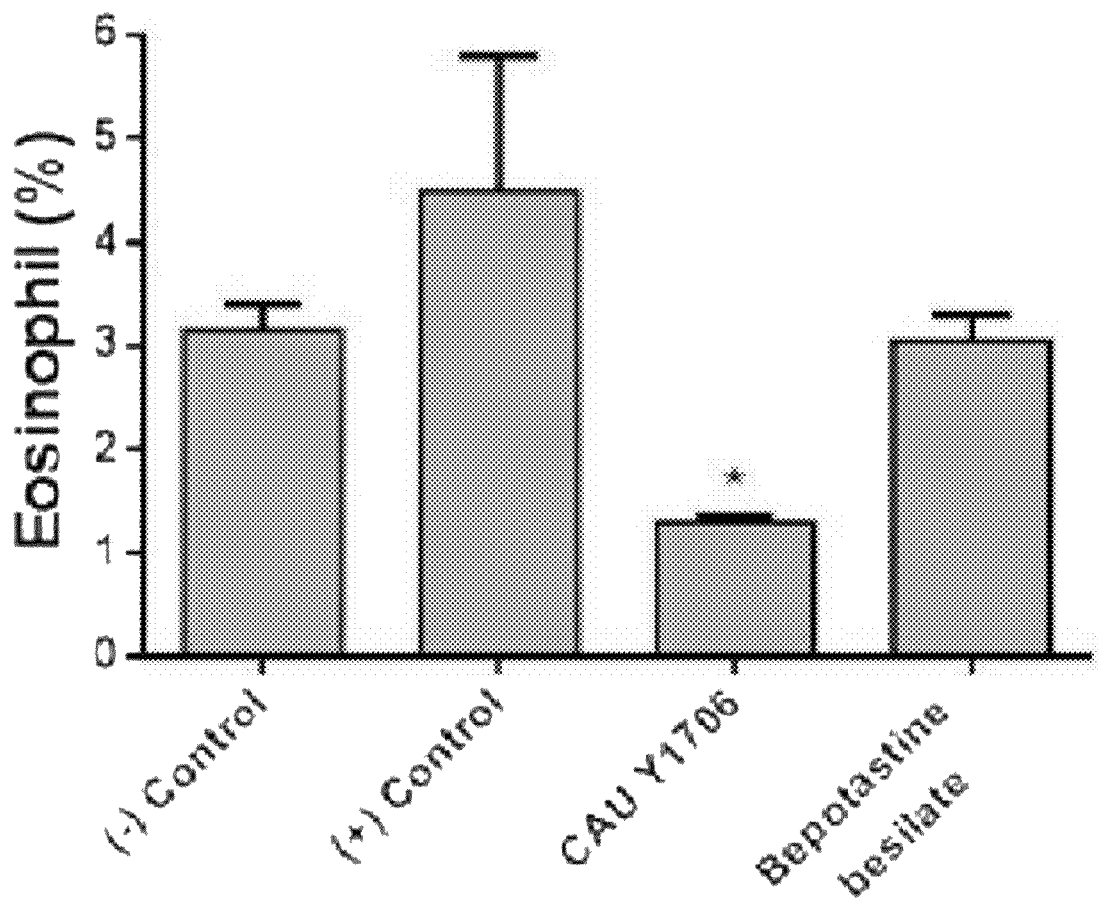
Figure 4C:
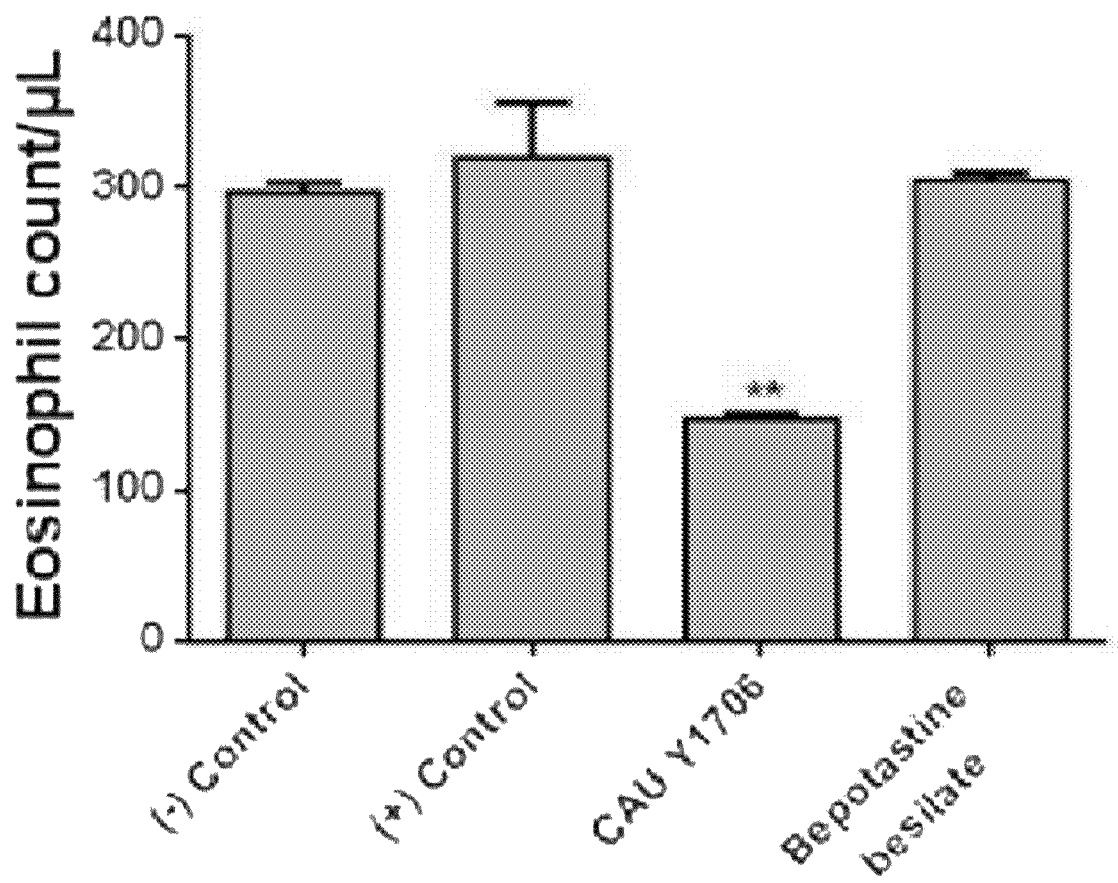
Figure 4D:
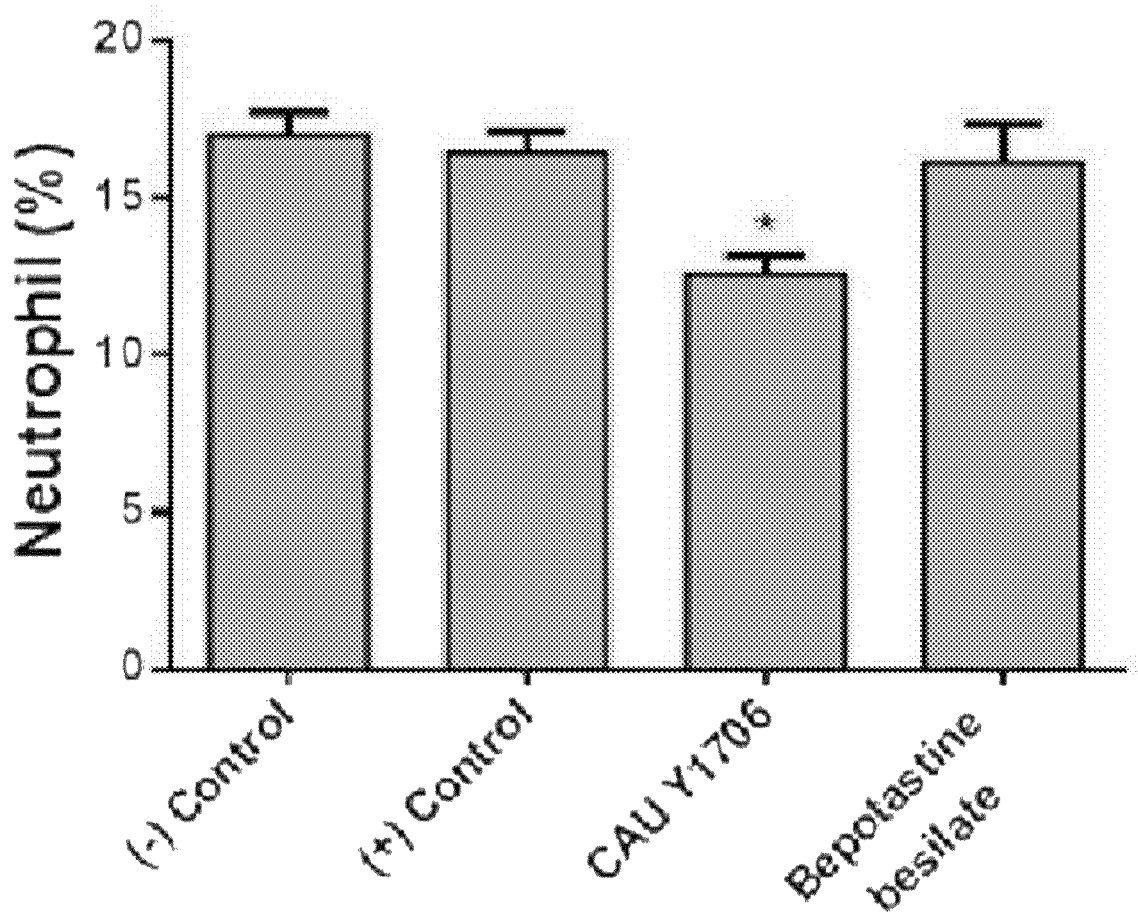
Figure 4E:
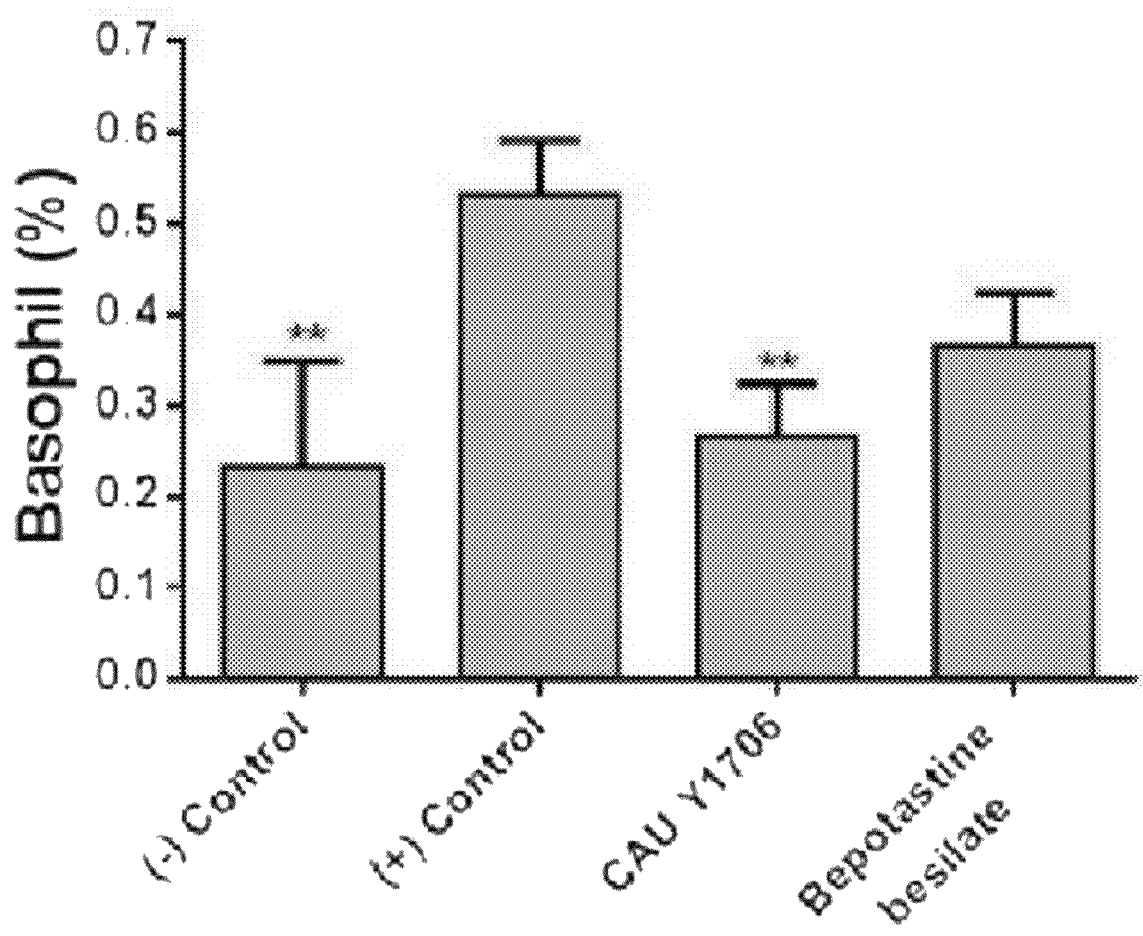

Example 3: Effects of *Kazachstania Turicensis* CAU Y1706 on IgE Levels in Blood and Serum Serum IgE levels were higher in the positive control group, and the *K. turicensis* CAU Y1706 administration group and the bepotastine besilate administration group showed significantly lower levels (FIG. 4a).

In addition, when comparing the positive control group, the group administered with bepotastine besilate and the group administered with *K. turicensis* CAU Y1706, it was confirmed that the number of eosinophils and the ratio of eosinophils, neutrophils, and basophils in the *K. turicensis* CAU Y1706 administration group were remarkably reduced (FIGS. 4b to 4e).

Figure 5A:
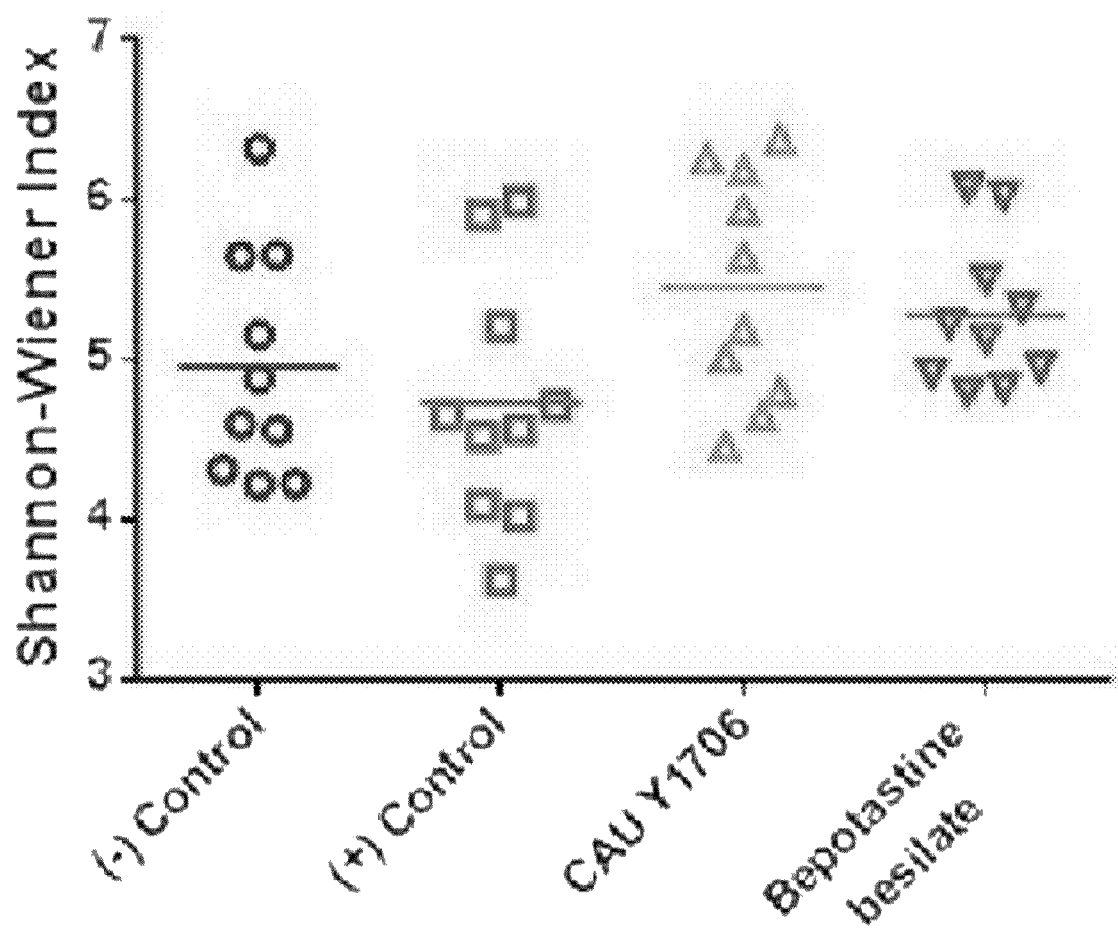
FIGS. 5A to 5H are results confirming that oral administration of *Kazachstania turicensis* CAU Y1706 contributes to the abundance and diversity of the intestinal microbial population of atopic dermatitis-induced mice.
Figure 5B:
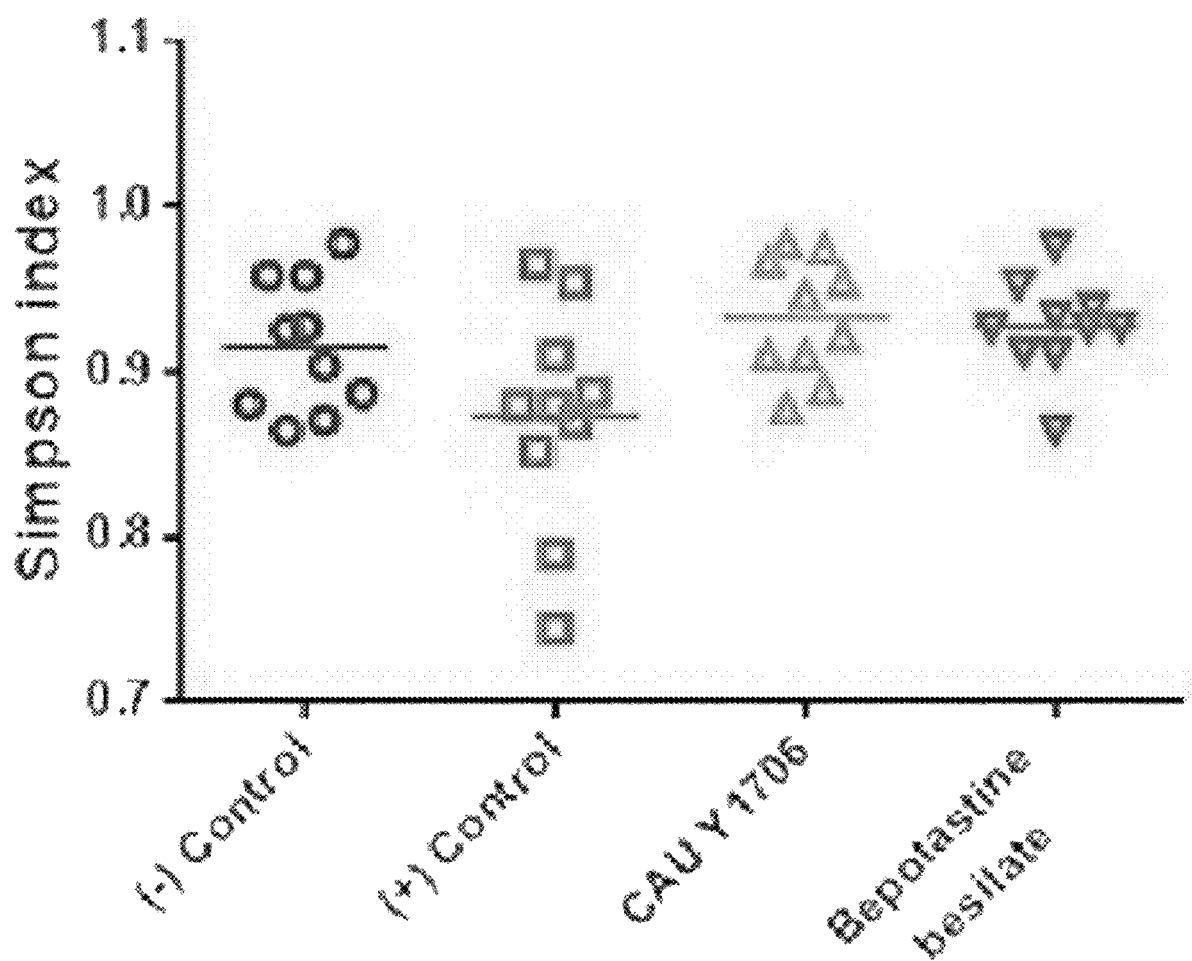
Figure 5C:
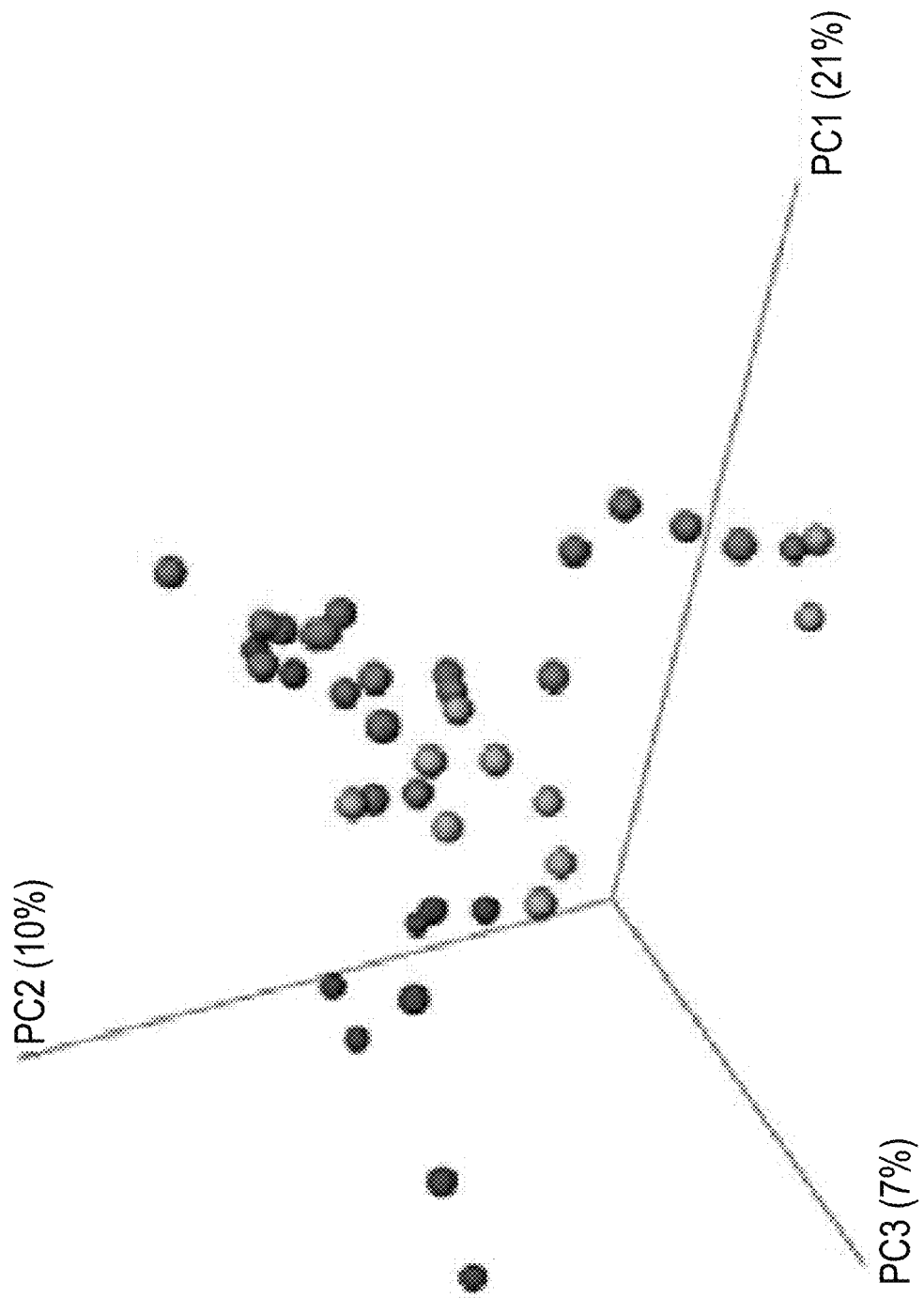

Example 4: Effects of *Kazachstania Turicensis* CAU Y1706 on the Regulation of Gut Microbiota To confirm the diversity of the intestinal microbiota, bacterial DNA was extracted from the fecal sample, and the 16S rRNA gene sequence was amplified through PCR. On average, 80.778 bacterial nucleotide sequences with an average length of 599 bp (±9.2 bp) were obtained per sample, a total of 3,231,137. The diversity and abundance of bacterial populations were statistically processed through operational taxonomic units (OTUs) (defined as 97%) and Shannon and Simpson indices (FIGS. 5a and 5b). Compared to the positive control group, the *K. turicensis* CAU Y1706 administration group showed superior abundance, uniformity, and diversity of intestinal microorganisms. Differences in the profiles of the gut microbiota at the genus level were evaluated through unweighted UniFrac-based 3D PCoA (FIG. 5c). These results show that the *K. turicensis* CAU Y1706 administration group had a significant difference compared to the positive control group.

Figure 5D:
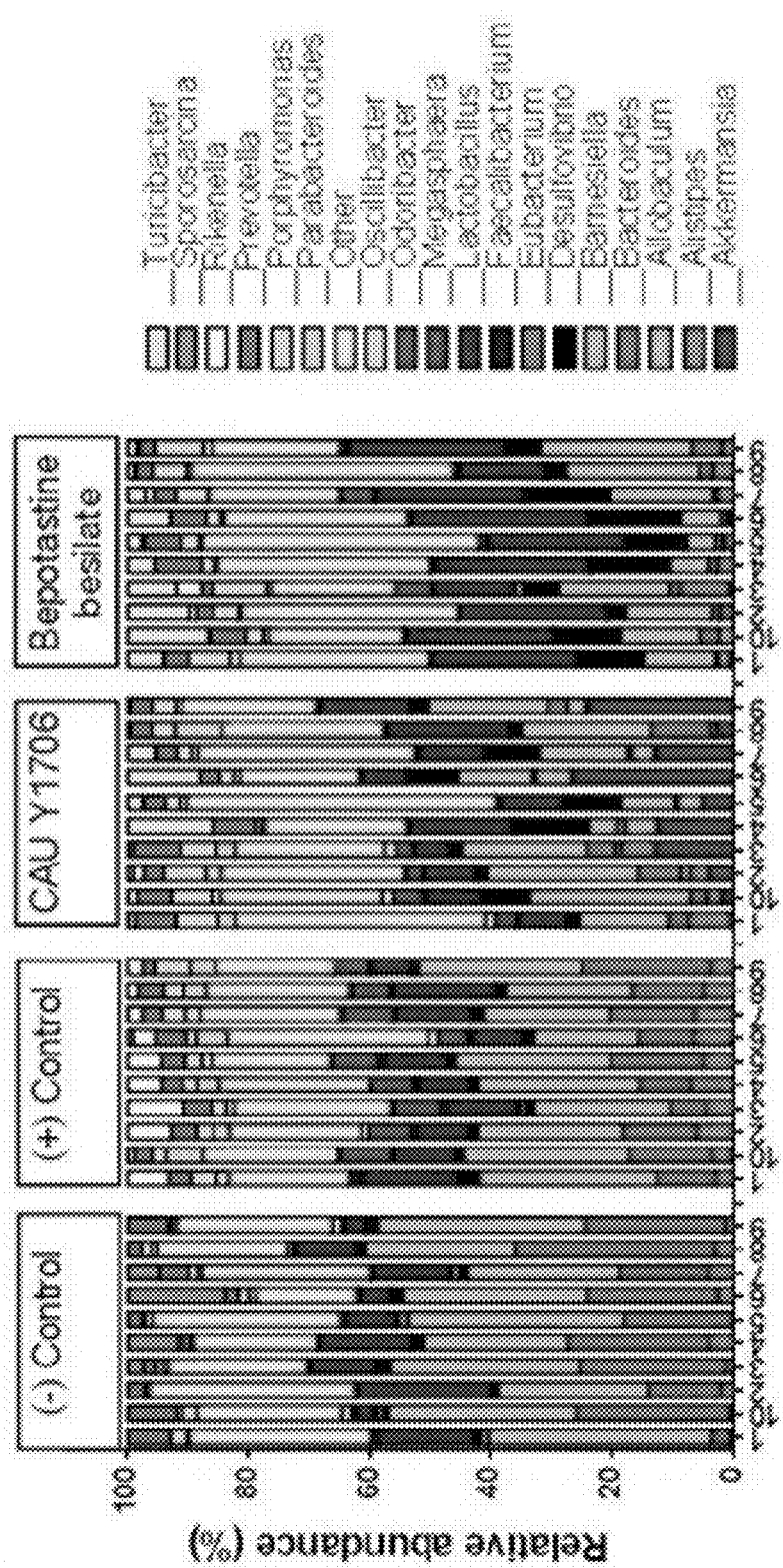
Figure 5E:
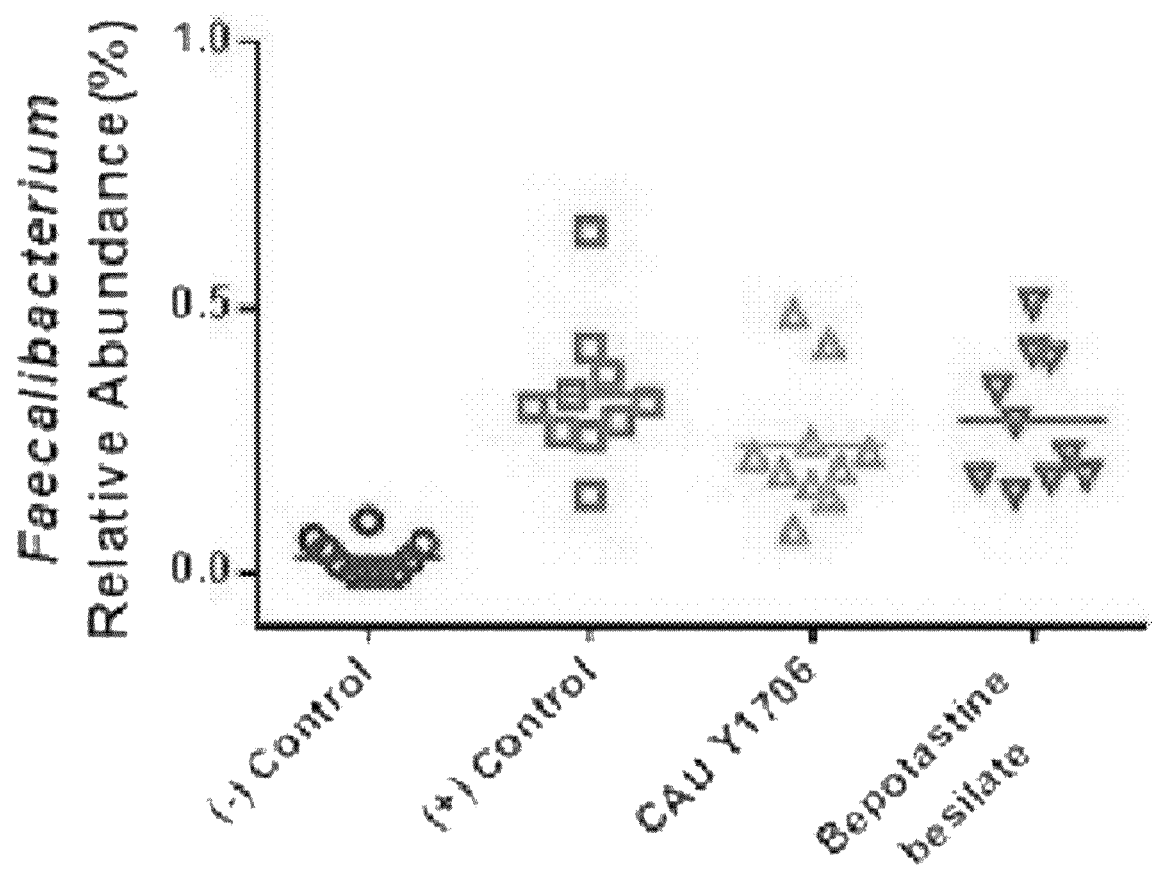
Figure 5F:
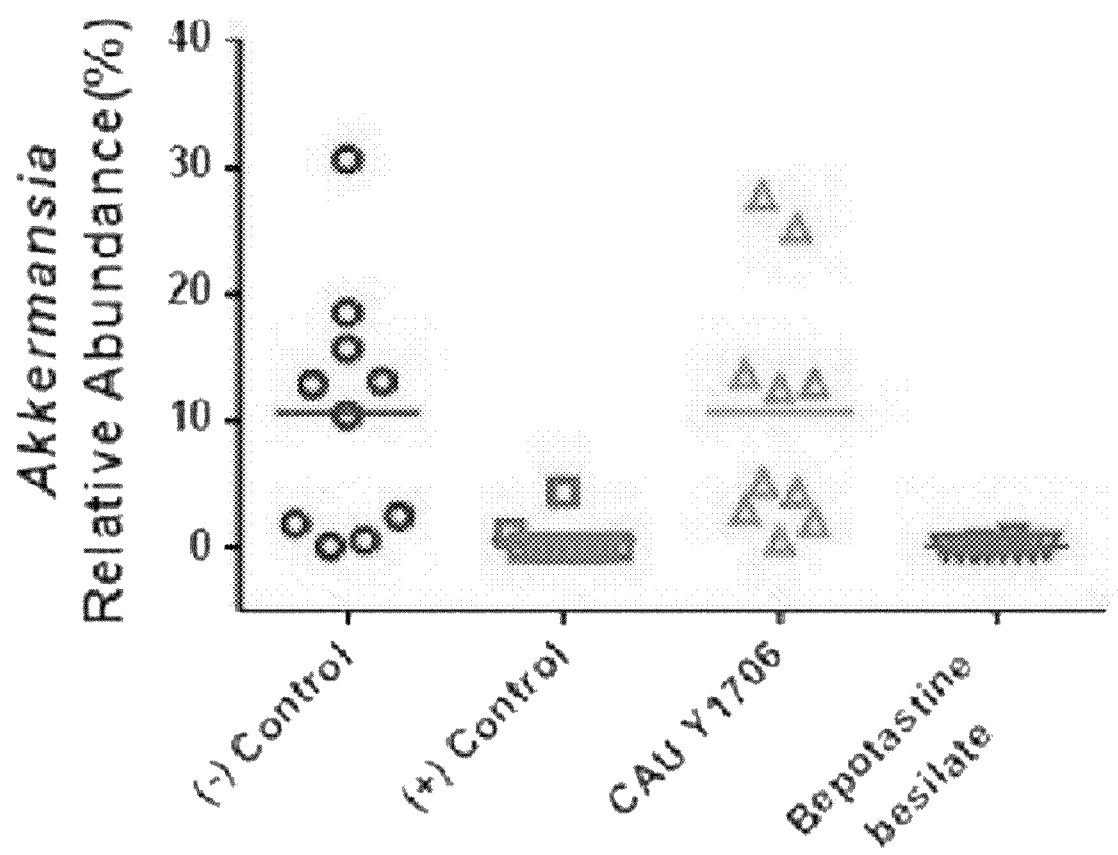
Figure 5G:
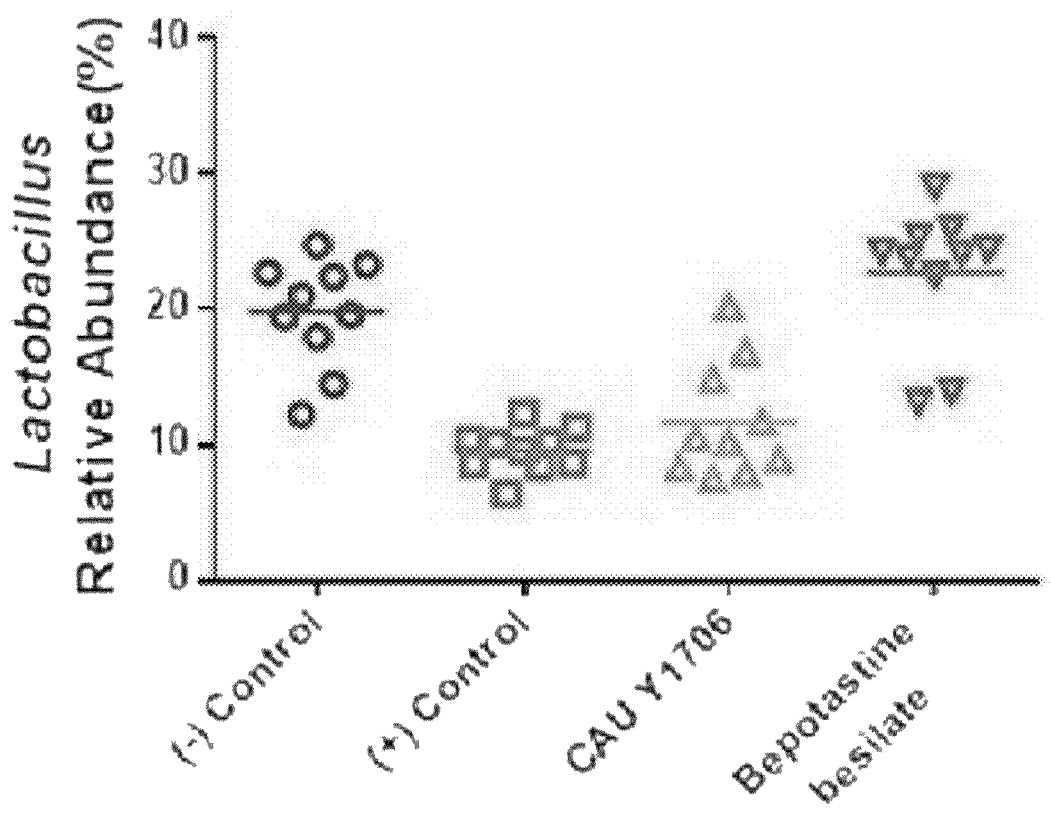
Figure 5H:
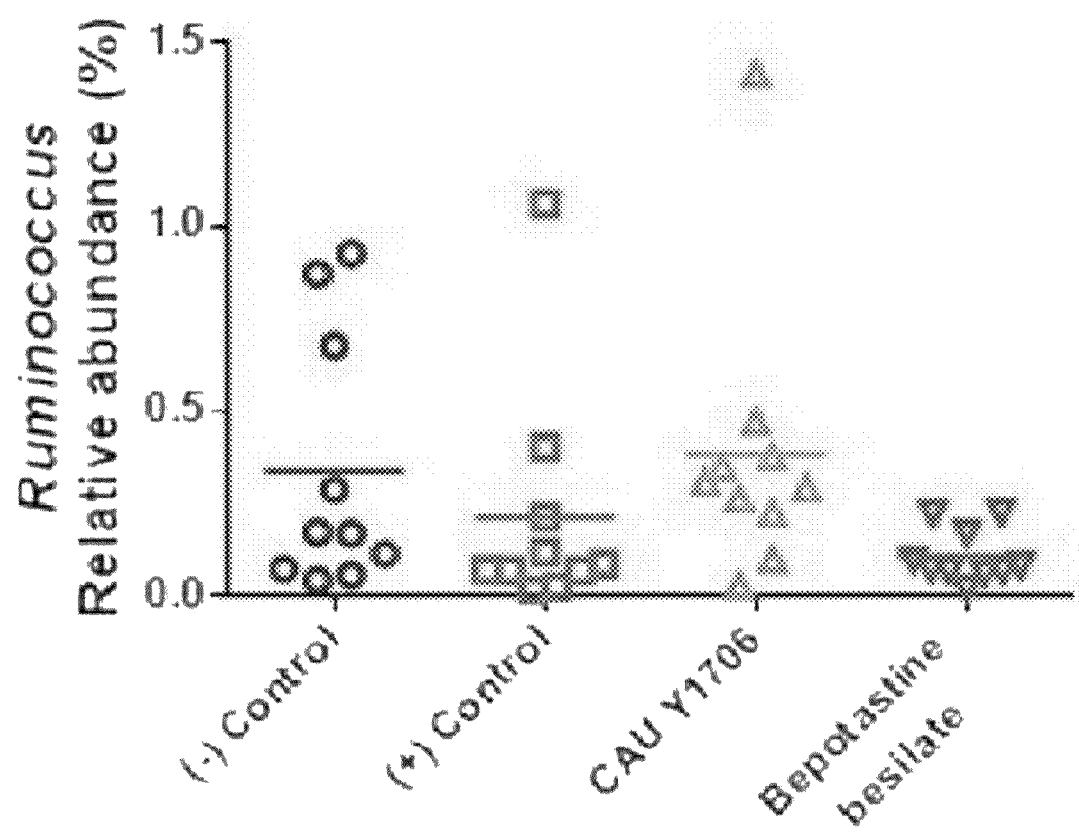

A total of 11 bacterial phyla were found when analyzed at the phylum level, and the three most dominant types were Firmicutes, Bacteroidetes, and Verrucomicrobia (FIG. 5d).

A total of 94 genera were found in the three types of phyla, of which four were found abundantly in all experimental groups (FIGS. 5e to 5h).

*Faecalibacterium* included in the genus Firmicutes was found to be lower in the negative control group and the *K. turicensis* CAU Y1706 administration group than in the positive control group ($p<0.0001$). Conversely, *Ruminococcus* showed higher levels in the negative control group and the *K. turicensis* CAU Y1706 administration group than in the positive control group ($p<0.05$).

*Akkermansia* of the Verrucomicrobia phylum was abundant in the negative control group and the *K. turicensis* CAU Y1706 administration group compared to the positive control group ($p<0.0001$). These results show that there is a difference in the intestinal microbial group including the abundance of genus taxonomic units between the positive control group and the *K. turicensis* CAU Y1706 administration group.

The gut microbiota is known to produce short chain fatty acids (SCFAs). SCFA Butyrate plays an important role in innate immunity, and has functions such as protection of intestinal health, anti-inflammatory effect, and promotion of Treg cell differentiation. Also, *Bacteroides, Ruminococcus*, and *Akkermansia* are known to produce butyrate, and *Lactobacillus* is known to be related to the promotion of butyrate production.

Therefore, as a result of oral administration of the yeast of the present invention, it was found that a variety of and abundant intestinal microflora that produce or promote butyrate production compared to the positive control group were found, and it was confirmed that the yeast of the present invention can be usefully used as a bowel preparation agent.

Example 5: Effects of *Kazachstania Turicensis* CAU Y1706 on Skin Inflammation and Intestines To verify the efficacy of *K. turicensis* CAU Y1706 on inflammation, evaluation and pathological analysis using the dermatitis score of OVA-sensitized mice administered *K. turicensis* CAU Y1706 were performed.

It was observed that the dermatitis score of the *K. turicensis* CAU Y1706 administration group was dramatically lower than that of the positive control group (FIG. 6a). These results indicate that *K. turicensis* CAU Y1706 is effective in improving skin lesions in atopic dermatitis mice.

In addition, local infiltration of mast cells in back skin cells and ileal lesions was confirmed by toluidine blue staining. In OVA-sensitized mice administered with *K. turicensis* CAU Y1706, it was observed that mast cell accumulation in both lesions was suppressed (FIGS. 6b and 6c).

Also, it was confirmed that the number of eosinophils was significantly lower in OVA-sensitized mice administered *K. turicensis* CAU Y1706 compared with the positive control group. When observing the skin lesion tissue stained with Congo red, it was observed that the eosinophil infiltration level of the *K. turicensis* CAU Y1706 administration group was reduced as in the bepotastine besilate administration group (FIG. 6d). These results show that *K. turicensis* CAU Y1706 has the effect of reducing the infiltration of mast cells and eosinophils in the back skin and ileum of atopic dermatitis mice.

Example 6: Acid Resistance Evaluation of *Kazachstania Turicensis* CAU Y1706

As an in vitro probiotic characterization test, acid resistance and bile resistance tests are widely used because it is necessary to have resistance to gastric juice and bile, which is necessary for a large number of bacteria to survive and reach the intestines stably in the human digestive system.

Therefore, in order to investigate the acid resistance of *Kazachstania turicensis* CAU Y1706, it was inoculated and cultured in TSB liquid medium titrated to pH 2.0 (Pancreatic digest of Casein 17 g/L, Papaic digest of Soybean 3 g/L, Dextrose 2.5 g/L, Sodium Chloride 5 g/L, Dipotassium Phosphate 2.5 g/L), and then the number of viable cells was measured. More specifically, after the *Kazachstania turicen-*

*sis* CAU Y1706 strain was inoculated in TSB broth, cultured at 30° C. for 12 hours, and the cells were recovered by centrifugation. After adjusting the $OD_{600}$ value to 1.0 with sterile water, 30 μl of the suspension was inoculated in a TSB liquid medium titrated to pH 2.0, and incubated for 0-120 minutes at 30° C., and then the number of viable cells was measured at A600 nm with Nanodrop (NanoQuant infinite M200, TECAN).

As shown in Table 1 of the experimental results, CAU Y1706 showed the ability to grow in MRS medium at pH 2.0 (same conditions as gastric juice). As for CAU Y1706, the number of bacteria increased at a significant rate as time passed, and as a result, it was confirmed that it was not inhibited under strong acid conditions. Therefore, it was confirmed that CAU Y1706 of the present invention has excellent acid resistance.

TABLE 1

| Time | Cell/ml ($10^6$) |
|---|---|
| 0 | 8.00 ± 0.00 |
| 15 | 12.43 ± 0.15 |
| 30 | 16.40 ± 0.26 |
| 60 | 20.07 ± 0.80 |
| 120 | 29.73 ± 0.11 |

Example 7: Evaluation of Bile Tolerance of *Kazachstania Turicensis* CAU Y1706

To test the resistance properties of *Kazachstania turicensis* CAU Y1706 to bile acids, bile acid (ox-bile dry pure, Merck, Germany) was inoculated and cultured in TSB liquid medium to which 0, 0.2 and 0.4% (w/v) were added, and then the number of viable cells were measured. More specifically, after the *Kazachstania turicensis* CAU Y1706 strain was inoculated in MRS liquid medium, cultured at 30° C. for 12 hours, and the cells were recovered by centrifugation. After adjusting the $OD_{600}$ value to 1.0 with sterile water, 30 μl of the suspension was inoculated in a TSB liquid medium containing 0, 0.2 and 0.4% bile acid and incubated for 0-12 hours at 30° C., and then the number of viable cells was measured at A600 nm with Nanodrop (NanoQuant infinite M200, TECAN).

As shown in Table 2 of the experimental results, *Kazachstania turicensis* CAU Y1706 showed the ability to grow in TSB medium supplemented with 0.2% or 0.4% bile, and the bacteria showed excellent growth ability in 0.2% and 0.4% bile. CAU Y1706 was confirmed to have high bile resistance (BTR) ability of 1.25 (0.2% bile condition) and 1.05 (0.4% bile condition) compared to the control group without the addition of bile. Therefore, through the above test, it was confirmed that the strain of the present invention can stably pass through the digestive tract, and a large number of bacteria can survive and reach the intestine.

[Accession Number]
Name of deposit institution: Korea Research Institute of Bioscience and Biotechnology
accession number: KCTC13794BP
deposit date: 20190122
Depositary address: (56212) Korea Research Institute of Bioscience and Biotechnology (KRIBB), 181, Ipsin-gil, Jeongeup-si, Jeollabuk-do, Republic of Korea

What is claimed is:

1. A method for treating an inflammatory disease comprising administering to a subject in need thereof an effective amount of a composition comprising *Kazachstania turicensis* CAU Y1706 (accession number: KCTC13794BP) strain or a culture thereof as an active ingredient.

2. The method of claim 1, wherein the *Kazachstania turicensis* CAU Y1706 (accession number: KCTC13794BP) has anti-inflammatory activity.

3. The method of claim 1, wherein the *Kazachstania turicensis* CAU Y1706 (accession number: KCTC13794BP) has acid resistance or bile resistance.

4. The method of claim 1, wherein the *Kazachstania turicensis* CAU Y1706 (accession number: KCTC13794BP) improves Th1/Th2 immune response imbalance.

5. The method of claim 1, wherein the inflammatory disease is any one selected from the group consisting of acute or chronic organ transplant rejection, graft-versus-host disease, inflammatory bowel disease, Crohn's disease, ulcerative colitis, inflammatory skin disease, multiple sclerosis, pancreatitis, trauma-induced shock, bronchial asthma, allergic rhinitis, allergic conjunctivitis, cystic fibrosis, acute bronchitis, chronic bronchitis, acute bronchiolitis, chronic bronchiolitis, osteoarthritis, gout, spondyloarthropathy, ankylosing spondylitis, Reiter's syndrome, psoriatic arthropathy, enteric spondylitis, juvenile arthritis, juvenile ankylosing spondylitis, reactive arthropathy, infectious arthritis, post-infectious arthritis, Lou Gehrig's disease, polyarteritis nodosa, hypersensitivity vasculitis, granulomatosis Lou Gehrig's disease, polymyalgia rheumatica, articular cell arteritis, calcium crystallization arthropathy, pseudo gout, non-articular rheumatism, bursitis, tendinitis, epicondylitis, neuropathic joint diseases (neuropathic joint disease or charcot joint), hemarthrosis, allergic purpura, hypertrophic osteoarthropathy, multicentral reticulocytoma, scoliosis, hemochromatosis, hemoglobinopathy, hyperproteinemia, hypogammaglobulinemia, familial Mediterranean fever, Behcet's disease, systemic lupus erythematosus, recurrent fever, sepsis, septic shock, acute respiratory distress syndrome, multiple organ failure, chronic obstructive pulmonary disease, rheumatoid arthritis, acute lung injury, broncho-pulmonary dysplasia, type 1 diabetes, type 2 diabetes, arteriosclerosis, Alzheimer's dementia, familial cold autoinflammatory syndrome, Muckle-Wells syndrome, neonatal multisystem inflammatory disease, chronic infantile neuro-

TABLE 2

Cell counts as log incubation time (h) of *Kazachstania turicensis* CAU Y1706

| Bile concentration (%) | 3 h | 6 h | 9 h | 12 h | BTR (Bile Tolerance Rate) |
|---|---|---|---|---|---|
| 0 | 4.13 ± 0.14 | 25.77 ± 0.06 | 44.60 ± 0.00 | 45.15 ± 0.05 | 1 |
| 0.2 | 7.27 ± 0.08 | 25.74 ± 0.06 | 46.13 ± 1.52 | 55.23 ± 0.06 | 1.25 |
| 0.4 | 5.57 ± 0.05 | 17.26 ± 0.42 | 46.20 ± 0.52 | 52.47 ± 0.06 | 1.05 | logic cutaneous articular syndrome, adult-onset Still's disease, contact dermatitis, hydatidiform mole, Pyogenic Arthritis, Pyoderma gangrenosum and Acne (PAPA) syndrome, hyperimmunoglobulin d syndrome, cryopyrin-associated periodic syndrome, keratitis, conjunctivitis, retinitis, retinal vasculitis, uveitis, blepharitis, dry eye, progressive systemic sclerosis, polymyositis, autoimmune encephalomyelitis, myasthenia gravis, polyarteritis nodosa and fibromyalgia syndrome.

6. The method of claim 5, wherein the inflammatory skin disease is any one selected from the group consisting of psoriasis, atopic dermatitis, dermatitis eczema, contact dermatitis, seborrheic dermatitis, pneumoconiosis rosacea, lichen planus, vasculitis, pityriasis pilaris, cellulitis, folliculitis, pemphigus, bullous pemphigus, epidermal blistering, urticaria, angioedema, erythema and cutaneous eosinophilia.

7. A method for improving an inflammatory disease comprising administering to a subject in need thereof an effective amount of a composition comprising *Kazachstania turicensis* CAU Y1706 (accession number: KCTC13794BP) strain or a culture thereof as an active ingredient.

8. A method for improving an inflammatory disease comprising applying to a subject in need thereof an effective amount of a cosmetic composition comprising *Kazachstania turicensis* CAU Y1706 (accession number: KCTC13794BP) strain or a culture thereof as an active ingredient.

9. The method of claim 7, wherein the composition is a food composition, probiotic composition, or an enteral composition.

10. A method of immunomodulation comprising administering to a subject in need thereof an effective amount of a composition comprising *Kazachstania turicensis* CAU Y1706 (accession number: KCTC13794BP) strain or a culture thereof as an active ingredient.

\* \* \* \* \*